United States Patent
Liu et al.

(10) Patent No.: US 9,708,592 B2
(45) Date of Patent: Jul. 18, 2017

(54) POLYPEPTIDES HAVING CELLULOLYTIC ENHANCING ACTIVITY AND POLYNUCLEOTIDES ENCODING SAME

(71) Applicants: Novozymes A/S, Bagsvaerd (DK); Novozymes, Inc., Davis, CA (US)

(72) Inventors: Ye Liu, Beijing (CN); Tarana Shaghasi, Dixon, CA (US); Matt Sweeney, Sacramento, CA (US)

(73) Assignees: Novosymes, Inc., Davis, CA (US); Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/430,867

(22) PCT Filed: Sep. 27, 2013

(86) PCT No.: PCT/CN2013/084473
§ 371 (c)(1),
(2) Date: Mar. 24, 2015

(87) PCT Pub. No.: WO2014/048369
PCT Pub. Date: Apr. 3, 2014

(65) Prior Publication Data
US 2015/0232825 A1    Aug. 20, 2015

(30) Foreign Application Priority Data

Sep. 28, 2012 (WO) ................ PCT/CN2012/082354

(51) Int. Cl.
| | | |
|---|---|---|
| *A01H 5/10* | (2006.01) | |
| *C12N 15/82* | (2006.01) | |
| *C12N 9/30* | (2006.01) | |
| *C12N 9/42* | (2006.01) | |
| *C12P 19/02* | (2006.01) | |
| *C12P 19/14* | (2006.01) | |

(52) U.S. Cl.
CPC ............ *C12N 9/2437* (2013.01); *C12P 19/02* (2013.01); *C12P 19/14* (2013.01); *C12P 2203/00* (2013.01); *C12Y 302/01004* (2013.01)

(58) Field of Classification Search
CPC .............................. C12N 9/244; C12N 9/2437
See application file for complete search history.

(56) References Cited

U.S. PATENT DOCUMENTS

| 8,138,321 | B2 * | 3/2012 | Bower | ...................... C12N 9/88 435/15 |
| 8,586,827 | B2 * | 11/2013 | Tang | ...................... C07K 14/37 424/93.2 |
| 2012/0237979 | A1 | 9/2012 | Duan et al. | |

OTHER PUBLICATIONS

Dimarogona et al (Bioresource Technology 110 (2012) 480-487).*
Horn et al (Biotechnology for Biofuels 2012, 5:45).*
Langston et al (Applied and Environmental Microbiology, Oct. 2011, p. 7007-7015).*
NCBI Reference Sequence: XP_001210534.1 (2008).*
Friedberg (Briefings in Bioinformatics. vol. 7. No. 3. 225^242).*
Petersen et al (Nature Methods, 8:785-786, 2011).*
SignalP Results (2016).*
Birren et al., Refseq Accession No. XP_001210534.

* cited by examiner

*Primary Examiner* — Lee A Visone
(74) *Attorney, Agent, or Firm* — Robert L. Starnes

(57) ABSTRACT

Provided are isolated polypeptides having cellulolytic enhancing activity, and polynucleotides encoding the polypeptides. Also provided are nucleic acid constructs, vectors and host cells comprising the polynucleotides as well as methods of producing and using polypeptides.

23 Claims, 3 Drawing Sheets

SEQUENCE LISTING

```
<160> NUMBER OF SEQ ID NOS: 10

<210> SEQ ID NO 1
<211> LENGTH: 1200
<212> TYPE: DNA
<213> ORGANISM: Aspergillus niveus

<400> SEQUENCE: 1
atgtctgtcg ctaagattgc tggtgtcgtc ctcggctctg cggcccttgt cgctggccac        60
ggttacgtct cgggtgccgt cgtcgatggc acgtactatg ccggttacga tgtcacctct       120
gccccttact ctaatgaccc tccggccacg atcggctggt cgacggatgc caccgacctc       180
ggcttcgttg acggcagcgc ctactccgac cctgacatca tctgccataa gaacgcccag       240
ccgggctcta tctctgctga agttgctgcc ggcagcgatg ttgagttgca gtggaccgaa       300
tggcccgaga gccaccacgg ccctgtcatt acctaccttg ccaactgcaa cggcgactgc       360
tcctcggtcg acaagacttc tctggagttc ttcaagatcg atcagaaggg tctcgttgat       420
gacagcgacg tccctggtac ctgggccagc gaccagctga tcagcagcaa caacagctgg       480
actgtcacca tccccagcag cattgcctcc ggcaactatg tcatgcgcca tgagattatt       540
gcgctccact ccgccggcaa caagaacggt gcccagaact accccagtg cctgaacttc        600 aaggttactg tggcggcag cgacaagccc tctggcaccc tcggtaccag cctgtacaag       660
gacactgacc ctggtatcct cgtcaacatc taccagactc tgtcctcgta cgtgatcccc       720
ggccctgccc tctactctgg cagctcttcc ggctctggct ctggctccgg ctctgccagc       780
tccagcgctg ctccctcggc cactccttcg ccttcctcca gcggtgtccc ctccagcacc       840
agcgtagccg tccctaccag ctctgccccg gctccctcgt tcaccaccgc cccgctcct        900 ccggctcaga ccagcactgc cactgcctac cagaccgcca ccacggtcga gagtgtcact       960
gtcaccgccg aggcgcccca gcagaccaag gtgcaggtcc ctaccgcgac cgtcccggct      1020
acccccggct ccacctctgg ctccagctcc ggctctggct ctgttcccac ccctagcggt      1080
```
agcagcagcc tctctgacta cttcaactcc ctgagcgccg agcagttcct gaacctgctc    1140
cgcgagactc tctcttggct gatcaccgac aagaagcacc cccgtgatat ctctgcctag    1200

<210> SEQ ID NO 2
<211> LENGTH: 399
<212> TYPE: PRT
<213> ORGANISM: Aspergillus niveus

<400> SEQUENCE: 2

Met Ser Val Ala Lys Ile Ala Gly Val Val Leu Gly Ser Ala Ala Leu
1               5                   10                  15

Val Ala Gly His Gly Tyr Val Ser Gly Ala Val Val Asp Gly Thr Tyr
            20                  25                  30

Tyr Ala Gly Tyr Asp Val Thr Ser Ala Pro Tyr Ser Asn Asp Pro Pro
        35                  40                  45

Ala Thr Ile Gly Trp Ser Thr Asp Ala Thr Asp Leu Gly Phe Val Asp
    50                  55                  60

Gly Ser Ala Tyr Ser Asp Pro Asp Ile Ile Cys His Lys Asn Ala Gln
65                  70                  75                  80

Pro Gly Ser Ile Ser Ala Glu Val Ala Ala Gly Ser Asp Val Glu Leu
                85                  90                  95

Gln Trp Thr Glu Trp Pro Glu Ser His His Gly Pro Val Ile Thr Tyr
            100                 105                 110

Leu Ala Asn Cys Asn Gly Asp Cys Ser Ser Val Asp Lys Thr Ser Leu
        115                 120                 125

Glu Phe Phe Lys Ile Asp Gln Lys Gly Leu Val Asp Asp Ser Asp Val
    130                 135                 140

Pro Gly Thr Trp Ala Ser Asp Gln Leu Ile Ser Ser Asn Asn Ser Trp
145                 150                 155                 160

Thr Val Thr Ile Pro Ser Ser Ile Ala Ser Gly Asn Tyr Val Met Arg
                165                 170                 175

His Glu Ile Ile Ala Leu His Ser Ala Gly Asn Lys Asn Gly Ala Gln
            180                 185                 190

Asn Tyr Pro Gln Cys Leu Asn Phe Lys Val Thr Gly Gly Gly Ser Asp
        195                 200                 205

Lys Pro Ser Gly Thr Leu Gly Thr Ser Leu Tyr Lys Asp Thr Asp Pro
    210                 215                 220

Gly Ile Leu Val Asn Ile Tyr Gln Thr Leu Ser Ser Tyr Val Ile Pro
225                 230                 235                 240

Gly Pro Ala Leu Tyr Ser Gly Ser Ser Gly Ser Gly Ser Gly Ser Gly
                245                 250                 255

Gly Ser Ala Ser Ser Ser Ala Ala Pro Ser Ala Thr Pro Ser Pro Ser
            260                 265                 270

Ser Ser Gly Val Pro Ser Ser Thr Ser Val Ala Val Pro Thr Ser Ser
        275                 280                 285

Ala Pro Ala Pro Ser Phe Thr Thr Ala Pro Ala Pro Ala Gln Thr
    290                 295                 300

Ser Thr Ala Thr Ala Tyr Gln Thr Ala Thr Val Glu Ser Val Thr
305                 310                 315                 320

Val Thr Ala Glu Ala Pro Gln Gln Thr Lys Val Gln Val Pro Thr Ala
                325                 330                 335

Thr Val Pro Ala Thr Pro Gly Ser Thr Ser Gly Ser Ser Ser Gly Ser
            340                 345                 350

Gly Ser Val Pro Thr Pro Ser Gly Ser Ser Ser Leu Ser Asp Tyr Phe

```
                      355                 360                 365
Asn Ser Leu Ser Ala Glu Gln Phe Leu Asn Leu Leu Arg Glu Thr Leu
            370                 375                 380

Ser Trp Leu Ile Thr Asp Lys Lys His Pro Arg Asp Ile Ser Ala
385                 390                 395

<210> SEQ ID NO 3
<211> LENGTH: 25
<212> TYPE: DNA
<213> ORGANISM: Aspergillus niveus

<400> SEQUENCE: 3
gctgtcatca acgagaccct tctga                                              25

<210> SEQ ID NO 4
<211> LENGTH: 19
<212> TYPE: DNA
<213> ORGANISM: Aspergillus niveus

<400> SEQUENCE: 4
tcgccgttgc agttggcaa                                                     19

<210> SEQ ID NO 5
<211> LENGTH: 42
<212> TYPE: DNA
<213> ORGANISM: Aspergillus niveus

<400> SEQUENCE: 5
acacaactgg ggatccacca tgtctgtcgc taagattgct gg                           42

<210> SEQ ID NO 6
<211> LENGTH: 41
<212> TYPE: DNA
<213> ORGANISM: Aspergillus niveus

<400> SEQUENCE: 6
gtcaccctct agatctggtc atactctcat cccatgatgg a                            41

<210> SEQ ID NO 7
<211> LENGTH: 1849
<212> TYPE: DNA
<213> ORGANISM: Trichoderma reesei

<400> SEQUENCE: 7
tgccatttct gacctggata ggttttccta tggtcattcc tataagagac acgctctttc        60
gtcggcccgt agatatcaga ttggtattca gtcgcacaga cgaaggtgag ttgatcctcc       120
aacatgagtt ctatgagccc ccccttgcc ccccccgtt caccttgacc tgcaatgaga         180
atcccacctt ttacaagagc atcaagaagt attaatggcg ctgaatagcc tctgctcgat       240
aatatctccc cgtcatcgac aatgaacaag tccgtggctc cattgctgct tgcagcgtcc      300
atactatatg gcggcgccgt cgcacagcag actgtctggg gccagtgtgg aggtattggt      360
tggagcggac ctacgaattg tgctcctggc tcagcttgtt cgaccctcaa tccttattat      420
gcgcaatgta ttccgggagc cactactatc accacttcga cccggccacc atccggtcca     480
accaccacca ccagggctac ctcaacaagc tcatcaactc acccacgag ctctggggtc      540 cgatttgccg cgttaacat cgcggggtttt gactttggct gtaccacaga gtgagtaccc    600
ttgtttcctg gtgttgctgg ctggttgggc gggtatacag cgaagcggac gcaagaacac    660
cgccggtccg ccaccatcaa gatgtgggtg gtaagcggcg gtgttttgta caactacctg    720
```

-continued

```
acagctcact caggaaatga gaattaatgg aagtcttgtt acagtggcac ttgcgttacc    780
tcgaaggttt atcctccgtt gaagaacttc accggctcaa acaactaccc cgatggcatc    840
ggccagatgc agcacttcgt caacgaggac gggatgacta ttttccgctt acctgtcgga    900
tggcagtacc tcgtcaacaa caatttgggc ggcaatcttg attccacgag catttccaag    960
tatgatcagc ttgttcaggg gtgcctgtct ctgggcgcat actgcatcgt cgacatccac   1020
aattatgctc gatggaacgg tgggatcatt ggtcagggcg ccctactaa tgctcaattc    1080
acgagccttt ggtcgcagtt ggcatcaaag tacgcatctc agtcgagggt gtggttcggc   1140
atcatgaatg agccccacga cgtgaacatc aacacctggg ctgccacggt ccaagaggtt   1200
gtaaccgcaa tccgcaacgc tggtgctacg tcgcaattca tctctttgcc tggaaatgat   1260
tggcaatctg ctggggcttt catatccgat ggcagtgcag ccgccctgtc tcaagtcacg   1320
aacccggatg ggtcaacaac gaatctgatt tttgacgtgc acaaatactt ggactcagac   1380
aactccggta ctcacgccga atgtactaca aataacattg acggcgcctt ttctccgctt   1440
gccacttggc tccgacagaa caatcgccag gctatcctga cagaaaccgg tggtggcaac   1500
gttcagtcct gcatacaaga catgtgccag caaatccaat atctcaacca gaactcagat   1560
gtctatcttg gctatgttgg ttggggtgcc ggatcatttg atagcacgta tgtcctgacg   1620
gaaacaccga ctggcagtgg taactcatgg acggacacat ccttggtcag ctcgtgtctc   1680
gcaagaaagt agcactctga gctgaatgca gaagcctcgc caacgtttgt atctcgctat   1740
caaacatagt agctactcta tgaggctgtc tgttctcgat ttcagcttta tatagtttca   1800
tcaaacagta catattccct ctgtggccac gcaaaaaaaa aaaaaaaaa                1849
```

<210> SEQ ID NO 8
<211> LENGTH: 418
<212> TYPE: PRT
<213> ORGANISM: Trichoderma reesei

<400> SEQUENCE: 8

```
Met Asn Lys Ser Val Ala Pro Leu Leu Ala Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175
```

Asp Gln Leu Val Gln Gly Cys Leu Ser Leu Gly Ala Tyr Cys Ile Val
            180                 185                 190

Asp Ile His Asn Tyr Ala Arg Trp Asn Gly Ile Ile Gly Gln Gly
            195                 200                 205

Gly Pro Thr Asn Ala Gln Phe Thr Ser Leu Trp Ser Gln Leu Ala Ser
210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
            275                 280                 285

Ala Ala Leu Ser Gln Val Thr Asn Pro Asp Gly Ser Thr Thr Asn Leu
            290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
            355                 360                 365

Tyr Leu Asn Gln Asn Ser Asp Val Tyr Leu Gly Tyr Val Gly Trp Gly
            370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys

<210> SEQ ID NO 9
<211> LENGTH: 3060
<212> TYPE: DNA
<213> ORGANISM: Aspergillus fumigatus

<400> SEQUENCE: 9
atgagattcg gttggctcga ggtggccgct ctgacggccg cttctgtagc caatgcccag        60
gtttgtgatg ctttcccgtc attgtttcgg atatagttga caatagtcat ggaaataatc       120
aggaattggc tttctctcca ccattctacc cttcgccttg ggctgatggc cagggagagt       180
gggcagatgc ccatcgacgc gccgtcgaga tcgtttctca tgacactg gcggagaagg       240 ttaaccttac aacgggtact gggtgggttg cgactttttt gttgacagtg agctttcttc       300
actgaccatc tacacagatg gaaatggac cgatgcgtcg gtcaaaccgg cagcgttccc       360
aggtaagctt gcaattctgc aacaacgtgc aagtgtagtt gctaaaacgc ggtggtgcag       420
acttggtatc aactgggtc tttgtggcca ggattcccct tgggtatcc gtttctgtga       480 gctataccg cggagtcttt cagtccttgt attatgtgct gatgattgtc tctgtatagc       540
tgacctcaac tccgccttcc ctgctggtac taatgtcgcc gcgacatggg acaagacact       600
cgcctacctt cgtggcaagg ccatgggtga ggaattcaac gacaagggcg tggacatttt       660
gctggggcct gctgctggtc tctcggcaa ataccccggac ggcggcagaa tctgggaagg       720

```
cttctctcct gatccggttc tcactggtgt acttttcgcc gaaactatca agggtatcca    780
agacgcgggt gtgattgcta ctgccaagca ttacattctg aatgaacagg agcatttccg    840
acaggttggc gaggcccagg gatatggtta acatcacg gagacgatca gctccaacgt     900
ggatgacaag accatgcacg agttgtacct ttggtgagta gttgacactg caaatgagga    960
ccttgattga tttgactgac ctggaatgca ggcccctttgc agatgctgtg cgcggtaaga  1020
ttttccgtag acttgacctc gcgacgaaga aatcgctgac gaaccatcgt agctggcgtt   1080
ggcgctgtca tgtgttccta caatcaaatc aacaacagct acggttgtca aaacagtcaa   1140
actctcaaca agctcctcaa ggctgagctg gcttccaag gcttcgtcat gagtgactgg    1200
agcgctcacc acagcggtgt cggcgctgcc ctcgctgggt tggatatgtc gatgcctgga   1260
gacatttcct tcgacgacgg actctccttc tggggcacga acctaactgt cagtgttctt   1320
aacggcaccg ttccagcctg gcgtgtcgat gacatggctg ttcgtatcat gaccgcgtac   1380
tacaaggttg gtcgtgaccg tcttcgtatt cccctaact tcagctcctg gacccgggat    1440
gagtacggct gggagcattc tgctgtctcc gagggagcct ggaccaaggt gaacgacttc   1500
gtcaatgtgc agcgcagtca ctctcagatc atccgtgaga ttggtgccgc tagtacagtg   1560
ctcttgaaga acacgggtgc tcttcctttg accggcaagg aggttaaagt gggtgttctc   1620
ggtgaagacg ctggttccaa cccgtggggt gctaacggct gccccgaccg cggctgtgat   1680
aacggcactc ttgctatggc ctggggtagt ggtactgcca acttcccta ccttgtcacc    1740
cccgagcagg ctatccagcg agaggtcatc agcaacggcg gcaatgtctt tgctgtgact   1800
gataacgggg ctctcagcca gatggcagat gttgcatctc aatccaggtg agtgcgggct   1860
cttagaaaaa gaacgttctc tgaatgaagt tttttaacca ttgcgaacag cgtgtctttg   1920
gtgtttgtca acgccgactc tggagagggt ttcatcagtg tcgacggcaa cgagggtgac   1980
cgcaaaaatc tcactctgtg gaagaacggc gaggccgtca ttgacactgt tgtcagccac   2040
tgcaacaaca cgattgtggt tattcacagt gttgggcccg tcttgatcga ccggtggtat   2100
gataacccca acgtcactgc catcatctgg gccggcttgc ccggtcagga gagtggcaac   2160
tccctggtcg acgtgctcta tggccgcgtc aaccccagcg ccaagacccc gttcacctgg   2220
ggcaagactc gggagtctta cggggctccc ttgctcaccg agcctaacaa tggcaatggt   2280
gctccccagg atgatttcaa cgagggcgtc ttcattgact accgtcactt tgacaagcgc   2340
aatgagaccc ccatttatga gtttggccat ggcttgagct acaccacctt tggttactct   2400
caccttcggg ttcaggccct caatagttcg agttcggcat atgtcccgac tagcggagag   2460
accaagcctg cgccaaccta tggtgagatc ggtagtgccg ccgactacct gtatcccgag   2520
ggtctcaaaa gaattaccaa gttttatttac ccttggctca actcgaccga cctcgaggat  2580
tcttctgacg acccgaacta cggctgggag gactcggagt acattcccga aggcgctagg   2640
gatgggtctc ctcaaccccct cctgaaggct ggcggcgctc ctggtggtaa ccctacccctt 2700
tatcaggatc ttgttagggt gtcggccacc ataaccaaca ctggtaacgt cgccggttat   2760
gaagtccctc aattggtgag tgacccgcat gttccttgcg ttgcaattttg gctaactcgc  2820
ttctagtatg tttcactggg cggaccgaac gagcctcggg tcgttctgcg caagttcgac   2880
cgaatcttcc tggctcctgg ggagcaaaag gtttggacca cgactcttaa ccgtcgtgat   2940
ctcgccaatt gggatgtgga ggctcaggac tgggtcatca caaagtaccc caagaaagtg   3000
cacgtcggca gctcctcgcg taagctgcct ctgagagcgc ctctgccccg tgtctactag   3060
```

<210> SEQ ID NO 10
<211> LENGTH: 863
<212> TYPE: PRT
<213> ORGANISM: Aspergillus fumigatus

<400> SEQUENCE: 10

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
    370                 375                 380
```

```
Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
            405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
            435                 440                 445

Ala Trp Gly Ser Gly Thr Ala Asn Phe Pro Tyr Leu Val Thr Pro Glu
            450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
            485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
            515                 520                 525

Lys Asn Gly Glu Ala Val Ile Asp Thr Val Val Ser His Cys Asn Asn
530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
            565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
            595                 600                 605

Gly Ala Pro Leu Leu Thr Glu Pro Asn Asn Gly Asn Gly Ala Pro Gln
            610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
            645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
            675                 680                 685

Gly Glu Ile Gly Ser Ala Ala Asp Tyr Leu Tyr Pro Glu Gly Leu Lys
            690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
            725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
            755                 760                 765

Ser Ala Thr Ile Thr Asn Thr Gly Asn Val Ala Gly Tyr Glu Val Pro
            770                 775                 780

Gln Leu Tyr Val Ser Leu Gly Gly Pro Asn Glu Pro Arg Val Val Leu
785                 790                 795                 800
```

-continued

```
Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
850                 855                 860
```

POLYPEPTIDES HAVING CELLULOLYTIC ENHANCING ACTIVITY AND POLYNUCLEOTIDES ENCODING SAME

CROSS-REFERENCE TO RELATED APPLICATIONS

This application is a 35 U.S.C. §371 national application of PCT/CN2013/084473 filed on Sep. 27, 2013, which claims priority or the benefit under 35 U.S.C. §119 of PCT/CN2012/082354 filed on Sep. 28, 2012, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having cellulolytic enhancing activity, and polynucleotides encoding the polypeptides. The invention also relates to nucleic acid constructs, vectors, and host cells comprising the polynucleotides as well as methods of producing and using the polypeptides.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

Once the cellulose is converted to glucose, the glucose can easily be fermented by yeast into ethanol.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin.

WO 2005/074647, WO 2008/148131, and WO 2011/035027 disclose isolated GH61 polypeptides having cellulolytic enhancing activity and the polynucleotides thereof from *Thielavia terrestris*. WO 2005/074656 and WO 2010/065830 disclose isolated GH61 polypeptides having cellulolytic enhancing activity and the polynucleotides thereof from *Thermoascus aurantiacus*. WO 2007/089290 and WO 2012/149344 disclose isolated GH61 polypeptides having cellulolytic enhancing activity and the polynucleotides thereof from *Trichoderma reesei*. WO 2009/085935, WO 2009/085859, WO 2009/085864, and WO 2009/085868 disclose isolated GH61 polypeptides having cellulolytic enhancing activity and the polynucleotides thereof from *Myceliophthora thermophila*. WO 2010/138754 discloses an isolated GH61 polypeptide having cellulolytic enhancing activity and the polynucleotide thereof from *Aspergillus fumigatus*. WO 2011/005867 discloses an isolated GH61 polypeptide having cellulolytic enhancing activity and the polynucleotide thereof from *Penicillium pinophilum*. WO 2011/039319 discloses an isolated GH61 polypeptide having cellulolytic enhancing activity and the polynucleotide thereof from *Thermoascus* sp. WO 2011/041397 discloses an isolated GH61 polypeptide having cellulolytic enhancing activity and the polynucleotide thereof from *Penicillium* sp. WO 2011/041504 discloses isolated GH61 polypeptides having cellulolytic enhancing activity and the polynucleotides thereof from *Thermoascus crustaceus*. WO 2012/030799 discloses isolated GH61 polypeptides having cellulolytic enhancing activity and the polynucleotides thereof from *Aspergillus aculeatus*. WO 2012/113340 discloses isolated GH61 polypeptides having cellulolytic enhancing activity and the polynucleotides thereof from *Thermomyces lanuginosus*. WO 2012/122477 discloses isolated GH61 polypeptides having cellulolytic enhancing activity and the polynucleotides thereof from *Aurantiporus alborubescens, Trichophaea saccata,* and *Penicillium thomii*. WO 2012/135659 discloses an isolated GH61 polypeptide having cellulolytic enhancing activity and the polynucleotide thereof from *Talaromyces stipitatus*. WO 2012/146171 discloses isolated GH61 polypeptides having cellulolytic enhancing activity and the polynucleotides thereof from *Humicola insolens*. WO 2012/101206 discloses isolated GH61 polypeptides having cellulolytic enhancing activity and the polynucleotides thereof from *Malbranchea cinnamomea, Talaromyces leycettanus,* and *Chaetomium thermophilum*. WO 2013/043910 discloses isolated GH61 polypeptides having cellulolytic enhancing activity and the polynucleotides thereof from *Acrophialophora fusispora* and *Corynascus sepedonium*. WO 2008/151043 and WO 2012/122518 disclose methods of increasing the activity of a GH61 polypeptide having cellulolytic enhancing activity by adding a divalent metal cation to a composition comprising the polypeptide.

There is a need in the art for new enzymes to increase efficiency and to provide cost-effective enzyme solutions for saccharification of cellulosic material.

The present invention provides GH61 polypeptides having cellulolytic enhancing activity and polynucleotides encoding the polypeptides.

SUMMARY OF THE INVENTION

The present invention relates to isolated polypeptides having cellulolytic enhancing activity selected from the group consisting of:

(a) a polypeptide having at least 75% sequence identity to the mature polypeptide of SEQ ID NO: 2;

(b) a polypeptide encoded by a polynucleotide that hybridizes under at least high stringency conditions with the mature polypeptide coding sequence of SEQ ID NO: 1 or the full-length complement thereof;

(c) a polypeptide encoded by a polynucleotide having at least 75% sequence identity to the mature polypeptide coding sequence of SEQ ID NO: 1;

(d) a variant of the mature polypeptide of SEQ ID NO: 2 comprising a substitution, deletion, and/or insertion at one or more (e.g., several) positions; and (e) a fragment of the polypeptide of (a), (b), (c), or (d) that has cellulolytic enhancing activity.

The present invention also relates to isolated polynucleotides encoding the polypeptides of the present invention; nucleic acid constructs, recombinant expression vectors, and recombinant host cells comprising the polynucleotides; and methods of producing the polypeptides.

The present invention also relates to processes for degrading a cellulosic material, comprising: treating the cellulosic material with an enzyme composition in the presence of a polypeptide having cellulolytic enhancing activity of the present invention.

The present invention also relates to processes of producing a fermentation product, comprising: (a) saccharifying a cellulosic material with an enzyme composition in the presence of a polypeptide having cellulolytic enhancing activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having cellulolytic enhancing activity of the present invention.

The present invention also relates to an isolated polynucleotide encoding a signal peptide comprising or consisting of amino acids 1 to 19 of SEQ ID NO: 2, which is operably linked to a gene encoding a protein, wherein the protein is foreign to the signal peptide; nucleic acid constructs, expression vectors, and recombinant host cells comprising the polynucleotides; and methods of producing a protein.

DEFINITIONS

Figure 1:
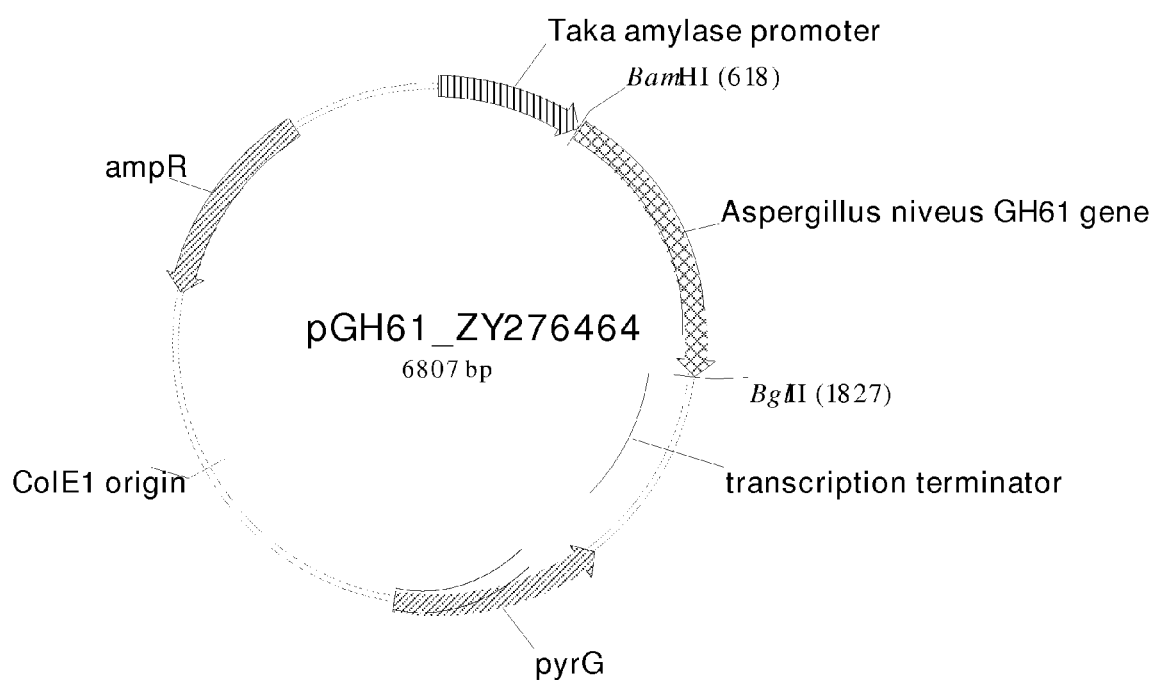
FIG. 1 shows a restriction map of pGH61_ZY276464.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 µmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 µmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, *J. Basic Microbiol.* 42: 55-66. One unit of beta-glucosidase is defined as 1.0 µmole of p-nitrophenolate anion produced per minute at 37° C., pH 5.0 from 1 mM p-nitrophenyl-beta-D-glucopyranoside as substrate in 100 mM succinic acid, 100 mM HEPES, 100 mM CHES, 100 mM CABS, 1 mM $CaCl_2$, 150 mM KCl, 0.01% TRITON® X-100 (4-(1,1,3,3-tetramethylbutyl)phenyl-polyethylene glycol).

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 µmole of p-nitrophenolate anion produced per minute at 40° C., pH 5 from 1 mM p-nitrophenyl-beta-D-xyloside in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by Lever et al., 1972, *Anal. Biochem.* 47: 273-279;

van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581. In the present invention, the Tomme et al. method can be used to determine cellobiohydrolase activity.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, *Pure Appl. Chem.* 59: 257-68).

For purposes of the present invention, cellulolytic enzyme activity is determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one aspect, the cellulosic material is any biomass material. In another aspect, the cellulosic material is lignocellulose, which comprises cellulose, hemicelluloses, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is arundo, bagasse, bamboo, corn cob, corn fiber, corn stover, miscanthus, rice straw, switchgrass, or wheat straw.

In another embodiment, the cellulosic material is aspen, eucalyptus, fir, pine, poplar, spruce, or willow.

In another embodiment, the cellulosic material is algal cellulose, bacterial cellulose, cotton linter, filter paper, microcrystalline cellulose (e.g., AVICEL®), or phosphoric-acid treated cellulose.

In another embodiment, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means a 4-(1, 3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24:

452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, *Biochem. J.* 280: 309-316, and Henrissat B., and Bairoch A., 1996, *Biochem. J.* 316: 695-696. The enzymes in this family were originally classified as a glycoside hydrolase family based on measurement of very weak endo-1,4-beta-D-glucanase activity in one family member. GH61 polypeptides are now classified as a lytic polysaccharide monooxygenase (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061) and placed into a new family designated "Auxiliary Activity 9" or "AA9".

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide; wherein the fragment has cellulolytic enhancing activity. In one aspect, a fragment contains at least 320 amino acid residues, e.g., at least 340 amino acid residues or at least 360 amino acid residues of SEQ ID NO: 2.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 399 of SEQ ID NO: 2 (P23N5M) based on the SignalP program (Nielsen et al., 1997, *Protein Engineering* 10: 1-6) that predicts amino acids 1 to 19 of SEQ ID NO: 2 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having cellulolytic enhancing activity. In one aspect, the mature polypeptide coding sequence is nucleotides 58 to 1197 of SEQ ID NO: 1 (D72BSG) based on the SignalP program (Nielsen et al., 1997, supra) that predicts nucleotides 1 to 57 of SEQ ID NO: 1 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of a polypeptide having cellulolytic enhancing activity for 1-7 days at a suitable temperature, such as 40° C.-80° C., e.g., 50° C., 55° C., 60° C., 65° C., or 70° C., and a suitable pH, such as 4-9, e.g., 4.5, 5.0, 5.5, 6.0, 6.5, 7.0, 7.5, 8.0, or 8.5, compared to a control hydrolysis with equal total protein loading without cellulolytic enhancing activity (1-50 mg of cellulolytic protein/g of cellulose in PCS).

GH61 polypeptide enhancing activity can be determined using a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 02/095014) of cellulase protein loading is used as the source of the cellulolytic activity.

GH61 polypeptide enhancing activity can also be determined by incubating the GH61 polypeptide with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X-100 for 24-96 hours at 40° C. followed by determination of the glucose released from the PASC GH61 polypeptide enhancing activity can also be determined according to WO 2013/028928 for high temperature compositions.

Alternatively, cellulolytic enhancing activity can also be determined according to Example 11 as described herein.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

The GH61 polypeptides of the present invention have at least 20%, e.g., at least 40%, at least 50%, at least 60%, at least 70%, at least 80%, at least 90%, at least 95%, and at least 100% of the cellulolytic enhancing activity of the mature polypeptide of SEQ ID NO: 2.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0, 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0, 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having cellulolytic enhancing activity. In one aspect, a subsequence contains at least 960 nucleotides, e.g., at least 1020 nucleotides or at least 1080 nucleotides of SEQ ID NO: 1.

Variant: The term "variant" means a polypeptide having cellulolytic enhancing activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrmann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 and 200 mM sodium phosphate pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6.

DETAILED DESCRIPTION OF THE INVENTION

Polypeptides Having Cellulolytic Enhancing Activity

In an embodiment, the present invention relates to isolated polypeptides having a sequence identity to the mature polypeptide of SEQ ID NO: 2 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellulolytic enhancing activity. In one aspect, the polypeptides differ by up to 10 amino acids, e.g., 1, 2, 3, 4, 5, 6, 7, 8, 9, or 10, from the mature polypeptide of SEQ ID NO: 2.

A polypeptide of the present invention preferably comprises or consists of the amino acid sequence of SEQ ID NO: 2 or an allelic variant thereof; or is a fragment thereof having cellulolytic enhancing activity. In another aspect, the polypeptide comprises or consists of the mature polypeptide of SEQ ID NO: 2. In another aspect, the polypeptide comprises or consists of amino acids 20 to 399 of SEQ ID NO: 2.

In another embodiment, the present invention relates to isolated polypeptides having cellulolytic enhancing activity encoded by polynucleotides that hybridize under very low stringency conditions, low stringency conditions, medium stringency conditions, medium-high stringency conditions, high stringency conditions, or very high stringency conditions with the mature polypeptide coding sequence of SEQ ID NO: 1, or the full-length complement thereof (Sambrook et al., 1989, *Molecular Cloning, A Laboratory Manual*, 2d edition, Cold Spring Harbor, N.Y.).

The polynucleotide of SEQ ID NO: 1, or a subsequence thereof, as well as the polypeptide of SEQ ID NO: 2, or a fragment thereof, may be used to design nucleic acid probes to identify and clone DNA encoding polypeptides having cellulolytic enhancing activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having cellulolytic enhancing activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, the mature polypeptide coding sequence thereof, or a subsequence thereof, the carrier material is used in a Southern blot.

For purposes of the present invention, hybridization indicates that the polynucleotides hybridize to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1 or the mature polypeptide coding sequence thereof.

In another embodiment, the present invention relates to isolated polypeptides having cellulolytic enhancing activity encoded by polynucleotides having a sequence identity to the mature polypeptide coding sequence of SEQ ID NO: 1 of at least at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2 comprising a substitution, deletion, and/or insertion at one or more (e.g., several) positions. In one aspect, the number of amino acid substitutions, deletions and/or insertions introduced into the mature polypeptide of SEQ ID NO: 2 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, thermal activity of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellulolytic enhancing activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Cellulolytic Enhancing Activity

A polypeptide having cellulolytic enhancing activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. In one aspect, the polypeptide is an *Aspergillus* polypeptide. In another aspect, the polypeptide is an *Aspergillus niveus* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

A polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Aspergillus*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, or the cDNA sequences thereof, by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the Bacillus amyloliquefaciens alpha-amylase gene (amyQ), Bacillus licheniformis alpha-amylase gene (amyL), Bacillus licheniformis penicillinase gene (penP), Bacillus stearothermophilus maltogenic amylase gene (amyM), Bacillus subtilis levansucrase gene (sacB), Bacillus subtilis xylA and xylB genes, Bacillus thuringiensis cryIIIA gene (Agaisse and Lereclus, 1994, Molecular Microbiology 13: 97-107), E. coli lac operon, E. coli trc promoter (Egon et al., 1988, Gene 69: 301-315), Streptomyces coelicolor agarase gene (dagA), and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25). Further promoters are described in "Useful proteins from recombinant bacteria" in Gilbert et al., 1980, Scientific American 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for Aspergillus nidulans acetamidase, Aspergillus niger neutral alpha-amylase, Aspergillus niger acid stable alpha-amylase, Aspergillus niger or Aspergillus awamori glucoamylase (glaA), Aspergillus oryzae TAKA amylase, Aspergillus oryzae alkaline protease, Aspergillus oryzae triose phosphate isomerase, Fusarium oxysporum trypsin-like protease (WO 96/00787), Fusarium venenatum amyloglucosidase (WO 00/56900), Fusarium venenatum Dana (WO 00/56900), Fusarium venenatum Quinn (WO 00/56900), Rhizomucor miehei lipase, Rhizomucor miehei aspartic proteinase, Trichoderma reesei beta-glucosidase, Trichoderma reesei cellobiohydrolase I, Trichoderma reesei cellobiohydrolase II, Trichoderma reesei endoglucanase I, Trichoderma reesei endoglucanase II, Trichoderma reesei endoglucanase III, Trichoderma reesei endoglucanase V, Trichoderma reesei xylanase I, Trichoderma reesei xylanase II, Trichoderma reesei xylanase III, Trichoderma reesei beta-xylosidase, and Trichoderma reesei translation elongation factor, as well as the NA2-tpi promoter (a modified promoter from an Aspergillus neutral alpha-amylase gene in which the untranslated leader has been replaced by an untranslated leader from an Aspergillus triose phosphate isomerase gene; non-limiting examples include modified promoters from an Aspergillus niger neutral alpha-amylase gene in which the untranslated leader has been replaced by an untranslated leader from an Aspergillus nidulans or Aspergillus oryzae triose phosphate isomerase gene); and mutant, truncated, and hybrid promoters thereof. Other promoters are described in U.S. Pat. No. 6,011,147.

In a yeast host, useful promoters are obtained from the genes for Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH1, ADH2/GAP), Saccharomyces cerevisiae triose phosphate isomerase (TPI), Saccharomyces cerevisiae metallothionein (CUP1), and Saccharomyces cerevisiae 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for Bacillus clausii alkaline protease (aprH), Bacillus licheniformis alpha-amylase (amyL), and Escherichia coli ribosomal RNA (rrnB).

Preferred terminators for filamentous fungal host cells are obtained from the genes for Aspergillus nidulans acetamidase, Aspergillus nidulans anthranilate synthase, Aspergillus niger glucoamylase, Aspergillus niger alpha-glucosidase, Aspergillus oryzae TAKA amylase, Fusarium oxysporum trypsin-like protease, Trichoderma reesei beta-glucosidase, Trichoderma reesei cellobiohydrolase I, Trichoderma reesei cellobiohydrolase II, Trichoderma reesei endoglucanase I, Trichoderma reesei endoglucanase II, Trichoderma reesei endoglucanase III, Trichoderma reesei endoglucanase V, Trichoderma reesei xylanase I, Trichoderma reesei xylanase II, Trichoderma reesei xylanase III, Trichoderma reesei beta-xylosidase, and Trichoderma reesei translation elongation factor.

Preferred terminators for yeast host cells are obtained from the genes for Saccharomyces cerevisiae enolase, Saccharomyces cerevisiae cytochrome C (CYC1), and Saccharomyces cerevisiae glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a Bacillus thuringiensis cryIIIA gene (WO 94/25612) and a Bacillus subtilis SP82 gene (Hue et al., 1995, Journal of Bacteriology 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for Aspergillus oryzae TAKA amylase and Aspergillus nidulans triose phosphate isomerase.

Suitable leaders for yeast host cells are obtained from the genes for Saccharomyces cerevisiae enolase (ENO-1), Saccharomyces cerevisiae 3-phosphoglycerate kinase, Saccharomyces cerevisiae alpha-factor, and Saccharomyces cerevisiae alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for Aspergillus nidulans anthranilate synthase, Aspergillus niger glucoamylase, Aspergillus niger alpha-glucosidase Aspergillus oryzae TAKA amylase, and Fusarium oxysporum trypsin-like protease.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for Bacillus NCIB 11837 maltogenic amylase, Bacillus licheniformis subtilisin, Bacillus licheniformis beta-lactamase, Bacillus stearothermophilus alpha-amylase, Bacillus stearothermophilus neutral proteases (nprT, nprS, nprM), and Bacillus subtilis prsA. Further signal peptides are described by Simonen and Palva, 1993, Microbiological Reviews 57: 109-137.

Effective signal peptide coding sequences for filamentous fungal host cells are the signal peptide coding sequences obtained from the genes for Aspergillus niger neutral amylase, Aspergillus niger glucoamylase, Aspergillus oryzae TAKA amylase, Humicola insolens cellulase, Humicola insolens endoglucanase V, Humicola lanuginosa lipase, and Rhizomucor miehei aspartic proteinase.

Useful signal peptides for yeast host cells are obtained from the genes for Saccharomyces cerevisiae alpha-factor and Saccharomyces cerevisiae invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for Bacillus subtilis alkaline protease (aprE), Bacillus subtilis neutral protease (nprT), Myceliophthora thermophila laccase (WO 95/33836), Rhizomucor miehei aspartic proteinase, and Saccharomyces cerevisiae alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the Aspergillus niger glucoamylase promoter, Aspergillus oryzae TAKA alpha-amylase promoter, and Aspergillus oryzae glucoamylase promoter, Trichoderma reesei cellobiohydrolase I promoter, and Trichoderma reesei cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are Bacillus licheniformis or Bacillus subtilis daI genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an Aspergillus cell are Aspergillus nidulans or Aspergillus oryzae amdS and pyrG genes and a Streptomyces hygroscopicus bar gene. Preferred for use in a Trichoderma cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive or Gram negative bacterium. Gram positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991,

*Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally (b) recovering the polypeptide. In one aspect, the cell is an *Aspergillus* cell. In another aspect, the cell is an *Aspergillus niveus* cell.

The present invention also relates to methods of producing a polypeptide of the present invention, comprising (a) cultivating a recombinant host cell of the present invention under conditions conducive for production of the polypeptide; and optionally (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a whole fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

Plants

The present invention also relates to isolated plants, e.g., a transgenic plant, plant part, or plant cell, comprising a polynucleotide of the present invention so as to express and produce a polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide may be constructed in accordance with methods known in the art. In short, the plant or plant cell is constructed by incorporating one or more expression constructs encoding the polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed (Sticklen, 2008, *Nature Reviews* 9: 433-443). For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising (a) cultivating a transgenic plant or a plant cell comprising a polynucleotide encoding the polypeptide under conditions conducive for production of the polypeptide; and optionally (b) recovering the polypeptide.

Removal or Reduction of Cellulolytic Enhancing Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may also be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having cellulolytic enhancing activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (sRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 1 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially cellulolytic enhancing activity-free product are of particular interest in the production of eukaryotic polypeptides, in particular fungal proteins such as enzymes. The cellulolytic enhancing activity-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from cellulolytic enhancing activity that is produced by a method of the present invention.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, an esterase, an expansin, a laccase, a ligninolytic enzyme, a pectinase, a catalase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Enzyme Compositions

The present invention also relates to compositions comprising a polypeptide of the present invention. Preferably, the compositions are enriched in such a polypeptide. The term "enriched" indicates that the cellulolytic enhancing activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, an esterase, an expansin, a laccase, a ligninolytic enzyme, a pectinase, a catalase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

Examples are given below of preferred uses of the compositions of the present invention. The dosage of the composition and other conditions under which the composition is used may be determined on the basis of methods known in the art.

Uses

The present invention is also directed to the following processes for using the polypeptides having cellulolytic enhancing activity, or compositions thereof.

The present invention also relates to processes for degrading a cellulosic material, comprising: treating the cellulosic material with an enzyme composition in the presence of a polypeptide having cellulolytic enhancing activity of the present invention. In one aspect, the processes further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition in the presence of a polypeptide having cellulolytic enhancing activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having cellulolytic enhancing activity of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel (ethanol, n-butanol, isobutanol, biodiesel, jet fuel) and/or platform chemicals (e.g., acids, alcohols, ketones, gases, oils, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd et al., 2002, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technology* 100: 10-18; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technology* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment.

Lime pretreatment is performed with calcium oxide or calcium hydroxide at temperatures of 85-150° C. and residence times from 1 hour to several days (Wyman et al., 2005, *Bioresource Technology* 96: 1959-1966; Mosier et al., 2005, *Bioresource Technology* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technology* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber expansion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.* 105-108: 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt. %, e.g., 20-70 wt. % or 30-60 wt. %, such as around 40 wt. %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition as described herein in the presence of a polypeptide having cellulolytic enhancing activity of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzymes(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 4.5 to about 5.5. The dry solids content is in the range of preferably about 5 to about 50 wt. %, e.g., about 10 to about 40 wt. % or about 20 to about 30 wt. %.

The enzyme compositions can comprise any protein useful in degrading the cellulosic material.

In one aspect, the enzyme composition comprises or further comprises one or more (e.g., several) proteins selected from the group consisting of a cellulase, a hemicellulase, an esterase, an expansin, a laccase, a ligninolytic enzyme, a pectinase, a catalase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a cellobiohydrolase I, a cellobiohydrolase II, or a combination of a cellobiohydrolase I and a cellobiohydrolase II. In another aspect, the enzyme composition comprises a beta-glucosidase. In another aspect, the enzyme composition comprises an endoglucanase and a cellobiohydrolase. In another aspect, the enzyme composition comprises an endoglucanase and a cellobiohydrolase I, a cellobiohydrolase II, or a combination of a cellobiohydrolase I and a cellobiohydrolase II. In another aspect, the enzyme composition comprises an endoglucanase and a beta-glucosidase. In another aspect, the enzyme composition comprises a beta-glucosidase and a cellobiohydrolase. In another aspect, the enzyme composition comprises a beta-glucosidase and a cellobiohydrolase I, a cellobiohydrolase II, or a combination of a cellobiohydrolase I and a cellobiohydrolase II. In another aspect, the enzyme composition comprises an endoglucanase, a beta-glucosidase, and a cellobiohydrolase. In another aspect, the enzyme composition comprises an endoglucanase, a beta-glucosidase, and a cellobiohydrolase I, a cellobiohydrolase II, or a combination of a cellobiohydrolase I and a cellobiohydrolase II.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In an embodiment, the xylanase is a Family 10 xylanase. In another embodiment, the xylanase is a Family 11 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a catalase. In another aspect, the enzyme composition comprises a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be native proteins, recombinant proteins, or a combination of native proteins and recombinant proteins. For example, one or more (e.g., several) components may be native proteins of a cell, which is used as a host cell to express recombinantly one or more (e.g., several) other components of the enzyme composition. It is understood herein that the recombinant proteins may be heterologous (e.g., foreign) and/or native to the host cell. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semipurified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and a polypeptide having cellulolytic enhancing activity depend on several factors including, but not limited to, the mixture of cellulolytic enzymes and/or hemicellulolytic enzymes, the cellulosic material, the concentration of cellulosic material, the pretreatment(s) of the cellulosic material, temperature, time, pH, and inclusion of a fermenting organism (e.g., for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a polypeptide having cellulolytic enhancing activity to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a polypeptide having cellulolytic enhancing activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material (collectively hereinafter "polypeptides having enzyme activity") can be derived or obtained from any suitable origin, including, archaeal, bacterial, fungal, yeast, plant, or animal origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained by, e.g., site-directed mutagenesis or shuffling.

A polypeptide having enzyme activity may be a bacterial polypeptide. For example, the polypeptide may be a Gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia,* or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having enzyme activity.

In another aspect, the polypeptide is a *Streptococcus equisimilis, Streptococcus pyogenes, Streptococcus uberis,* or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus,* or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces,* or *Yarrowia* polypeptide having enzyme activity; or more preferably a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host can be a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST™ (Novozymes A/S), NOVOZYM™

188 (Novozymes A/S), SPEZYME™ CP (Genencor Int.), ACCELERASE™ TRIO (DuPont), FILTRASE® NL (DSM); METHAPLUS® S/L 100 (DSM), ROHAMENT™ 7069 W (Röhm GmbH), or ALTERNAFUEL® CMAX3™ (Dyadic International, Inc.). The cellulolytic enzyme preparation is added in an amount effective from about 0.001 to about 5.0 wt. % of solids, e.g., about 0.025 to about 4.0 wt. % of solids or about 0.005 to about 2.0 wt. % of solids.

Examples of bacterial endoglucanases that can be used in the processes of the present invention, include, but are not limited to, *Acidothermus cellulolyticus* endoglucanase (WO 91/05039; WO 93/15186; U.S. Pat. No. 5,275,944; WO 96/02551; U.S. Pat. No. 5,536,655; WO 00/70031; WO 05/093050), *Erwinia carotovara* endoglucanase (Saarilahti et al., 1990, *Gene* 90: 9-14), *Thermobifida fusca* endoglucanase III (WO 05/093050), and *Thermobifida fusca* endoglucanase V (WO 05/093050).

Examples of fungal endoglucanases that can be used in the present invention, include, but are not limited to, *Trichoderma reesei* endoglucanase I (Penttila et al., 1986, *Gene* 45: 253-263, *Trichoderma reesei* Cel7B endoglucanase I (GenBank:M15665), *Trichoderma reesei* endoglucanase II (Saloheimo et al., 1988, *Gene* 63:11-22), *Trichoderma reesei* Cel5A endoglucanase II (GenBank: M19373), *Trichoderma reesei* endoglucanase III (Okada et al., 1988, *Appl. Environ. Microbiol.* 64: 555-563, GenBank: AB003694), *Trichoderma reesei* endoglucanase V (Saloheimo et al., 1994, *Molecular Microbiology* 13: 219-228, GenBank:Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Fusarium oxysporum* endoglucanase (GenBank:L29381), *Humicola grisea* var. *thermoidea* endoglucanase (GenBank:AB003107), *Melanocarpus albomyces* endoglucanase (GenBank:MAL515703), *Neurospora crassa* endoglucanase (GenBank:XM_324477), *Humicola insolens* endoglucanase V, *Myceliophthora thermophila* CBS 117.65 endoglucanase, *Thermoascus aurantiacus* endoglucanase I (GenBank:AF487830) and *Trichoderma reesei* strain No. VTT-D-80133 endoglucanase (GenBank:M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Penicillium occitanis* cellobiohydrolase I (GenBank:AY690482), *Talaromyces emersonii* cellobiohydrolase I (GenBank:AF439936), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 02/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Other useful endoglucanases, cellobiohydrolases, and beta-glucosidases are disclosed in numerous Glycosyl Hydrolase families using the classification according to Henrissat, 1991, *Biochem. J.* 280: 309-316, and Henrissat and Bairoch, 1996, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In one aspect, the polypeptide having cellulolytic enhancing activity is used in the presence of a soluble activating divalent metal cation according to WO 2008/151043, e.g., manganese or copper.

In another aspect, the polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl) furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), DEPOL™ 762P (Biocatalysts Limit, Wales, UK), ALTERNA FUEL 100P (Dyadic), and ALTERNA FUEL 200P (Dyadic).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Talaromyces lanuginosus* GH11 (WO 2012/130965), *Talaromyces thermophilus* GH11 (WO 2012/13095), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt:Q7SOW4), Trichoderma reesei (UniProtKB/TrEMBL:Q92458), *Talaromyces emersonii* (SwissProt:Q8X212), and *Talaromyces thermophilus* GH11 (WO 2012/13095).

Examples of acetylxylan esterases useful in the processes of the present invention include, but are not limited to, acetylxylan esterases from *Aspergillus aculeatus* (WO 2010/108918), *Chaetomium globosum* (UniProt:Q2GWX4), *Chaetomium gracile* (GeneSeqP:AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt:q7s259), *Phaeosphaeria nodorum* (UniProt:QOUHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt:A1 D9T4), *Neurospora crassa* (UniProt:Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP:AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt: alcc12), *Aspergillus fumigatus* (SwissProt:Q4WW45), *Aspergillus niger* (UniProt:Q96WX9), *Aspergillus terreus* (SwissProt:Q0CJ P9), *Humicola insolens* (WO 2010/014706), *Penicillium* aurantiogriseum (WO 2009/068565), *Talaromyces emersonii* (UniProt:Q8X211), and *Trichoderma reesei* (UniProt:Q99024).

In a preferred embodiment, the enzyme composition is a high temperature composition, i.e., a composition that is able to hydrolyze a cellulosic material in the range of about 55° C. to about 70° C. In another preferred embodiment, the enzyme composition is a high temperature composition, i.e., a composition that is able to hydrolyze a cellulosic material at a temperature of about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., or about 70° C. In another preferred embodiment, the enzyme composition is a high temperature composition, i.e., a composition that is able to hydrolyze a cellulosic material at a temperature of at least 55° C., at least 56° C., at least 57° C., at least 58° C., at least 59° C., at least 60° C., at least 61° C., at least 62° C., at least 63° C., at least 64° C., at least 65° C., at least 66° C., at least 67° C., at least 68° C., at least 69° C., or at least 70° C.

In another preferred embodiment, the enzyme composition is a high temperature composition as disclosed in WO 2011/057140, which is incorporated herein in its entirety by reference.

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous.

Any suitable hydrolyzed cellulosic material can be used in the fermentation step in practicing the present invention. The material is generally selected based on economics, i.e., costs per equivalent sugar potential, and recalcitrance to enzymatic conversion.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Yeast include strains of *Candida, Kluyveromyces,* and *Saccharomyces*, e.g., *Candida sonorensis, Kluyveromyces marxianus,* and *Saccharomyces cerevisiae.*

Examples of fermenting organisms that can ferment pentose sugars in their native state include bacterial and fungal organisms, such as some yeast. Xylose fermenting yeast include strains of *Candida*, preferably *C. sheatae* or *C. sonorensis*; and strains of *Pichia*, e.g., *P. stipitis*, such as *P. stipitis* CBS 5773. Pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae*; *Clostridium*, such as *C. acetobutylicum, C. thermocellum*, and *C. phytofermentans*; *E. coli* especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus, K. lactis, K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In an aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, *Appl. Biochem. Biotechnol.* 39-40: 135-147; Ho et al., 1998, *Appl. Environ. Microbiol.* 64: 1852-1859; Kotter and Ciriacy, 1993, *Appl. Microbiol. Biotechnol.* 38: 776-783; Walfridsson et al., 1995, *Appl. Environ. Microbiol.* 61: 4184-4190; Kuyper et al., 2004, *FEMS Yeast Research* 4: 655-664; Beall et al., 1991, *Biotech. Bioeng.* 38: 296-303; Ingram et al., 1998, *Biotechnol. Bioeng.* 58: 204-214; Zhang et al., 1995, *Science* 267: 240-243; Deanda et al., 1996, *Appl. Environ. Microbiol.* 62: 4465-4470; WO 03/062430).

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In one aspect, the fermentation product is an alcohol. It will be understood that the term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, World *Journal of Microbiology and Biotechnology* 19(6): 595-603.

In another aspect, the fermentation product is an alkane. The alkane may be an unbranched or a branched alkane. The alkane can be, but is not limited to, pentane, hexane, heptane, octane, nonane, decane, undecane, or dodecane.

In another aspect, the fermentation product is a cycloalkane. The cycloalkane can be, but is not limited to, cyclopentane, cyclohexane, cycloheptane, or cyclooctane.

In another aspect, the fermentation product is an alkene. The alkene may be an unbranched or a branched alkene. The alkene can be, but is not limited to, pentene, hexene, heptene, or octene.

In another aspect, the fermentation product is an amino acid. The organic acid can be, but is not limited to, aspartic acid, glutamic acid, glycine, lysine, serine, or threonine. See, for example, Richard and Margaritis, 2004, *Biotechnology and Bioengineering* 87(4): 501-515.

In another aspect, the fermentation product is a gas. The gas can be, but is not limited to, methane, $H_2$, $CO_2$, or CO. See, for example, Kataoka et al., 1997, *Water Science and Technology* 36(6-7): 41-47; and Gunaseelan, 1997, *Biomass and Bioenergy* 13(1-2): 83-114.

In another aspect, the fermentation product is isoprene.

In another aspect, the fermentation product is a ketone. It will be understood that the term "ketone" encompasses a substance that contains one or more ketone moieties. The ketone can be, but is not limited to, acetone.

In another aspect, the fermentation product is an organic acid. The organic acid can be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptide

The present invention also relates to an isolated polynucleotide encoding a signal peptide comprising or consisting of amino acids 1 to 19 of SEQ ID NO: 2. The polynucleotide may further comprise a gene encoding a protein, which is operably linked to the signal peptide. The protein is preferably foreign to the signal peptide. In one aspect, the polynucleotide encoding the signal peptide is nucleotides 1 to 57 of SEQ ID NO: 1.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and optionally (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The gene may be obtained from any prokaryotic, eukaryotic, or other source.

The present invention is further described by the following examples that should not be construed as limiting the scope of the invention.

EXAMPLES

Strain

*Aspergillus niveus* strain NN046949 was isolated from a soil from Yunnan Province, China by directly plating the soil sample onto a PDA plate followed by incubation at 37° C. for 5 days. The strain was then purified by transferring the mycelia onto a YG agar plate. The *Aspergillus niveus* strain was identified as *Aspergillus niveus* based on both morphological and molecular (ITS sequencing) characterization.

Media

COVE trace elements solution was composed of 0.04 g of $Na_2B_4O_7.10H_2O$, 0.4 g of $CuSO_4.5H_2O$, 1.2 g of $FeSO4.7H_2O$, 0.7 g of $MnSO_4.H_2O$, 0.8 g of $Na_2MoO_2.2H_2O$, 10 g of $ZnSO_4.7H_2O$, and deionized water to 1 liter.

Minimal medium plates were composed of 6 g of $NaNO_3$, 0.52 g of KCl, 1.52 g of $KH_2PO_4$, 1 ml of COVE trace elements solution, 20 g of Noble agar, 20 ml of 50% glucose, 2.5 ml of $MgSO_4.7H_2O$, 20 ml of a 0.02% biotin solution, and deionized water to 1 liter.

NNCYP-PCS medium was composed of 5 g of $NaNO_3$, 3 g of $NH_4Cl$, 2.0 g of MES, 2.5 g of citric acid, 0.2 g of $CaCl_2$ $2H_2O$, 1 g of Bacto Peptone, 5 g of yeast extract, 0.2 g of $MgSO_4$ $7H_2O$, 4 g of $K_2HPO_4$, 1 ml of COVE trace elements solution, 2.5 g of glucose, 25 g of pretreated corn stover (PCS), and deionized water to 1 liter.

PDA plates were composed of 39 grams of potato dextrose agar and deionized water to 1 liter.

YG agar plates were composed of 5.0 g of yeast extract, 10.0 g of glucose, 20.0 g of agar, and deionized water to 1 liter.

YPM medium was composed of 1% yeast extract, 2% of peptone, and 2% of maltose in deionized water.

Example 1: Preparation of *Aspergillus niveus* Mycelia for cDNA Sequencing

*Aspergillus niveus* was inoculated onto a PDA plate and incubated for 4 days at 37° C. in the darkness. Several mycelia-PDA plugs were inoculated into 500 ml shake flasks containing 100 ml of NNCYP-PCS medium. The flasks were incubated for 6 days at 37° C. with shaking at 160 rpm. The mycelia were collected at 4, 5, and 6 days, and each frozen in liquid nitrogen and stored at −80° C. freezer until use.

Example 2: *Aspergillus niveus* RNA Preparation

The frozen *Aspergillus niveus* mycelia were mixed and transferred into a liquid nitrogen prechilled mortar and pestle and ground to a fine powder. Total RNA was prepared from the powdered mycelia of each day by extraction with TRIZOL® reagent (Invitrogen, Carlsbad, Calif., USA) and purified using a RNEASY® Mini Kit (QIAGEN GmbH, Hilden, Germany). The polyA enriched RNA was isolated using a mTRAP™ Total Kit (Active Motif, Carlsbad, Calif., USA). Eighty-seven µg of total RNA were submitted for sequencing as described in Example 3.

Example 3: Sequence Assembly and Mining

Total RNA enriched for polyA sequences with the mRNASeq protocol (Illumina, Inc., San Diego, Calif., USA) was sequenced using an ILLUMINA® GA2 System (Illumina, Inc., San Diego, Calif., USA). The raw 75 base pair reads were assembled with SOAPdenovo (Li et al., 2010, *Genome Research* 20(2): 265-72). The assembled sequences were analyzed using standard bioinformatics methods for gene finding and functional prediction. Briefly, ESTscan 2.0 (Lottaz et al., 2003, *Bioinformatics* 19: ii103-ii112) was used for gene prediction. NCBI blastall version 2.2.10 (Altschul et al., 1990, *J. Mol. Biol.* 215 (3): 403-410; National Center for Biotechnology Information (NCBI), Bethesda, Md., USA) and HMMER version 2.1.1 (Eddy, 1998, *Bioinformatics* 14(9): 755-763; National Center for Biotechnology Information (NCBI), Bethesda, Md., USA) were used to predict function based on structural homology. The GH61 family gene was identified as a partial sequence by analysis of the Blast results.

Example 4: Cloning of the Flanking Region, 5' End, of the Partial cDNA Sequence of the *Aspergillus niveus* GH61 Polypeptide Coding Sequence from Genomic DNA

*Aspergillus niveus* was grown on a PDA plate at 37° C. for 3 days. Mycelia were collected directly from the agar plate into a sterilized mortar and frozen under liquid nitrogen. Frozen mycelia were ground, by mortar and pestle, to a fine powder, and genomic DNA was isolated using a DNEASY® Plant Mini Kit (QIAGEN GmbH, Hilden, Germany).

Based on the partial cDNA sequence of the *Aspergillus niveus* GH61 gene obtained in Example 3, oligonucleotide primers, shown below, were designed to clone the 5' end of the *Aspergillus niveus* GH61 gene using a DNA WALKING SPEEDUP™ Premix Kit (Seegene Inc., Seoul, Korea). The DNA WALKING SPEEDUP™ Premix Kit allows the identification of unknown sequences adjacent to upstream or downstream known sequences. Three PCR steps were performed as described below.
Primer ZY276464as1:
5'-GCTGTCATCAACGAGACCCTTCTGA-3' (SEQ ID NO: 3)
Primer ZY276464as2:
5'-TCGCCGTTGCAGTTGGCAA-3' (SEQ ID NO: 4)

In the first PCR step, four reactions were performed in 4 individual PCR tubes each containing 10 picomoles of one of the 4 sense primers, DW-ACP1, DW-ACP2, DW-ACP3 and DW-ACP4, provided by the DNA WALKING SPEEDUP™ Premix Kit and 10 picomoles of primer ZY276464as1 as the antisense primer. One of the PCR reactions also contained 2 µl of *Aspergillus niveus* genomic DNA, 25 µl of 2X SEEAMP™ ACP™ Master Mix II (Seegene Inc., Seoul, Korea), and deionized water to a final volume of 50 µl. The reactions were named according to the sense primer used, such as reaction 1 meaning DW-ACP1 was used and so on. The amplification was performed using a Peltier Thermal Cycler (MJ Research Inc., South San Francisco, Calif., USA) programmed for denaturing at 94° C. for 5 minutes; annealing at 42° C. for 1 minute and elongation at 72° C. for 2 minutes; 10 cycles each at 94° C. for 30 seconds, 60° C. for 30 seconds, with a 1° C. decrease per cycle, and 72° C. for 2 minutes; 25 cycles each at 94° C. for 30 seconds, 50° C. for 30 seconds, and 72° C. for 2 minutes; and a final extension at 72° C. for 10 minutes. The heat block then went to a 4° C. soak cycle. The first step PCR reactions were then diluted 5-fold by addition of deionized water and used as the templates in the second PCR step reactions.

In the second PCR step, 4 new PCR reactions were performed. For each individual reaction, 1 µl of the corresponding diluted PCR solution from the first step was added as the template. The PCR reaction was also composed of 10 µl of 2X SEEAMP™ ACP™ Master Mix II, 1 µl of 10 µM DW-ACPN provided by the DNA WALKING SPEEDUP™ Premix Kit, 1 µl of 10 µM primer ZY276464as2, and deionized water to a final volume of 20 µl. The amplification was performed using a Peltier Thermal Cycler programmed for 1 cycle at 94° C. for 3 minutes; 10 cycles each at 94° C. for 30 seconds, 65° C. for 30 seconds, with a 1° C. decrease per cycle, and 72° C. for 2 minutes; 25 cycles each at 94° C. for 30 seconds, 55° C. for 30 seconds, and 72° C. for 2 minutes; and a final extension at 72° C. for 10 minutes. The heat block then went to a 15° C. soak cycle.

In the third PCR step, another 4 new PCR reactions were performed. For each individual reaction, 1 µl of the corresponding PCR reaction solution from the second step was added as the template. The PCR reaction was also composed of 10 µl of 2× SEEAMP™ ACP™ Master Mix II, 1 µl of 10 µM Universal primer provided by the DNA WALKING SPEEDUP™ Premix Kit, 1 µl of 10 µM primer ZY276464as2, and deionized water to a final volume of 20 µl. The amplification was performed using a Peltier Thermal Cycler programmed for 1 cycle at 94° C. for 3 minutes; 10 cycles each at 94° C. for 30 seconds, 65° C. for 30 seconds, with a 1° C. decrease per cycle, and 72° C. for 2 minutes; 25 cycles each at 94° C. for 30 seconds, 55° C. for 30 seconds, and 72° C. for 2 minutes; and a final extension at 72° C. for 10 minutes. The heat block then went to a 15° C. soak cycle.

The 4 PCR reactions were analyzed by 1.0% agarose gel electrophoresis using 90 mM Tris-borate and 1 mM EDTA (TBE) buffer where an approximately 800 bp product band was observed in reaction 2 of the third step. This PCR product band was isolated by electrophoresis again, excised from the gel, and purified using an ILLUSTRA™ GFX™ PCR DNA and Gel Band Purification Kit (GE Healthcare, Buckinghamshire, UK) according to the manufacturer's instructions. The sequence of the PCR product was determined by DNA sequencing using a 3730XL DNA Analyzer (Applied Biosystems Inc, Foster City, Calif., USA), which showed that the PCR product was the 5' flanking region of the partial sequence obtained in Example 3 where the start site was identified by sequence comparison.

Example 5: Cloning of the *Aspergillus niveus* GH61 Polypeptide Coding Sequence and Construction of an *Aspergillus oryzae* Expression Vector Based on the 5' end sequence obtained in Example 4 and the cDNA sequence in Example 3, the following 2 primers were designed to amplify the GH61 gene from the genomic DNA of *Aspergillus niveus*. An IN-FUSION® CF Dry-down Cloning Kit (Clontech Laboratories, Inc., Mountain View, Calif., USA) was used to clone the fragment directly into the expression vector pPFJO355 (WO 2011/005867), without the need for restriction digestion and ligation.

```
Forward primer:
                                      (SEQ ID NO: 5)
5'-ACACAACTGGGGATCCACCatgtctgtcgctaagattgctgg-3'

Reverse primer:
                                      (SEQ ID NO: 6)
5'-GTCACCCTCTAGATCTggtcatactctcatcccatgatgga-3'
```

The lower case letters in the forward primer represent the coding sequence of the gene and in the reverse primer represent the downstream region sequence of the gene. The upper case letters represent sequences that are homologous to the insertion sites of pPFJO355.

Twenty picomoles of each of the primers above were used in a PCR reaction composed of *Aspergillus niveus* genomic DNA, 10 μl of 5X PHUSION® GC Buffer (Finnzymes Oy, Espoo, Finland), 1.5 μl of DMSO, 2 μl of 2.5 mM dATP, dTTP, dGTP, and dCTP, and 0.6 unit of PHUSION® High-Fidelity DNA Polymerase (Finnzymes Oy, Espoo, Finland) in a final volume of 50 μl. The amplification was performed using a Peltier Thermal Cycler programmed for denaturing at 98° C. for 1 minute; 7 cycles of denaturing at 98° C. for 15 seconds, annealing at 66° C. for 30 seconds, with a 1° C. decrease per cycle, and elongation at 72° C. for 1 minute; 21 cycles each at 98° C. for 15 seconds, 63° C. for 30 seconds, and 72° C. for 1 minute; and a final extension at 72° C. for 5 minutes. The heat block then went to a 4° C. soak cycle.

The reaction products were isolated by 1.0% agarose gel electrophoresis using TBE buffer where an approximately 1.2 kb product band was excised from the gel, and purified using an ILLUSTRA™ GFX™ PCR DNA and Gel Band Purification Kit according to the manufacturer's instructions.

Plasmid pPFJO355 was digested with Bam HI and Bgl II, isolated by 1.0% agarose gel electrophoresis using TBE buffer, and purified using an ILLUSTRA™ GFX™ PCR DNA and Gel Band Purification Kit according to the manufacturer's instructions.

The gene fragment and the digested vector were ligated together using an IN-FUSION® CF Dry-down PCR Cloning Kit (Clontech Laboratories, Inc., Mountain View, Calif., USA) resulting in pGH61_ZY276464 (FIG. 1) in which transcription of the *Aspergillus niveus* GH61 polypeptide coding sequence was under the control of an *Aspergillus oryzae* alpha-amylase gene promoter. In brief, 30 ng of pPFJO355 digested with Bam HI and Bgl II, and 50 ng of the *Aspergillus niveus* GH61 gene purified PCR product were added to a reaction vial to a final volume of 10 μl by addition of deionized water. The reaction was incubated at 37° C. for 15 minutes followed by 50° C. for 15 minutes. Three μl of the reaction were used to transform *E. coli* TOP10 competent cells (TIANGEN Biotech (Beijing) Co. Ltd., Beijing, China). An *E. coli* transformant containing pGH61_ZY276464 was detected by colony PCR. Briefly, a single colony was transferred to a premixed PCR solution in a PCR tube, including PCR buffer, MgCl$_2$, dNTPs, and primer pairs from which the PCR fragment was generated. Totally 7-10 colonies were screened. After the PCR, the reactions were analyzed by 1.0% agarose gel electrophoresis using TBE buffer. Plasmid DNA was prepared from colonies showing an insert with the expected size using a QIAPREP® Spin Miniprep Kit (QIAGEN GmbH, Hilden, Germany). The *Aspergillus niveus* GH61 polypeptide coding sequence in pGH61_ZY276464 was confirmed by DNA sequencing using a 3730XL DNA Analyzer (Applied Biosystems Inc, Foster City, Calif., USA).

Example 6: Characterization of the *Aspergillus niveus* GH61 Polypeptide and Coding Sequence Thereof The genomic DNA sequence and deduced amino acid sequence of the *Aspergillus niveus* GH61 polypeptide are shown in SEQ ID NO: 1 (D72BSG) and SEQ ID NO: 2 (P23N5M), respectively. The coding sequence is 1200 bp including the stop codon. The encoded predicted protein is 399 amino acids. Using the SignalP program (Nielsen et al., 1997, supra), a signal peptide of 19 residues was predicted. The SignalP prediction is in accord with the necessity for having a histidine reside at the N-terminus in order for proper metal binding and hence protein function to occur (See Harris et al., 2010, *Biochemistry* 49: 3305, and Quinlan et al., 2011, *Proc. Natl. Acad. Sci. USA* 108: 15079). The predicted mature protein contains 380 amino acids with a predicted molecular mass of 38.213 kDa and a predicted isoelectric point of 4.40.

A comparative pairwise global alignment of amino acid sequences was determined using the Needleman and Wunsch algorithm (Needleman and Wunsch, 1970, supra) with a gap open penalty of 10, a gap extension penalty of 0.5, and the EBLOSUM62 matrix. The alignment showed that the deduced amino acid sequence of the *Aspergillus niveus* DNA encoding a GH61 polypeptide shares 71.5% sequence identity (excluding gaps) to the deduced amino acid sequence of a GH61 polypeptide from *Aspergillus aculeatus* (GENESEQP:AZW46090).

Example 7: Expression of *Aspergillus niveus* GH61 Polypeptide Coding Sequence in *Aspergillus oryzae*

*Aspergillus oryzae* HowB101 (WO 95/35385, Example 1) protoplasts were prepared according to the method of Christensen et al., 1988, Bio/Technology 6: 1419-1422, and transformed with 3 μg of pGH61_ZY276464. The transformation yielded approximately 50 transformants. Four transformants were isolated to individual Minimal medium plates.

The four transformants were inoculated separately into 3 ml of YPM medium in a 24-well plate and incubated at 30° C. with agitation at 150 rpm. After 3 days incubation, 20 μl of supernatant from each culture were analyzed by SDS-PAGE using a NUPAGE® NOVEX® 4-12% Bis-Tris Gel with 2-(N-morpholino)ethanesulfonic acid (MES) buffer (Invitrogen Corporation, Carlsbad, Calif., USA) according to the manufacturer's instructions. The resulting gel was stained with INSTANTBLUE™ (Expedeon Ltd., Babraham Cambridge, UK). SDS-PAGE profiles of the cultures showed that the majority of the transformants had a smeary band at approximately 70 kDa. The expression strain was designated *Aspergillus oryzae* EXP03643.

Example 8: Fermentation *Aspergillus oryzae* Expression Strain EXP03643

A slant of *Aspergillus oryzae* EXP03643 was washed with 10 ml of YPM medium and inoculated into four 2-liter flasks containing 400 ml of YPM medium to generate broth for characterization of the enzyme. The culture was harvested on day 3 and filtered using a 0.45 μm DURAPORE® Membrane (Millipore, Bedford, Mass., USA).

A 1600 ml volume of the filtered broth of *Aspergillus oryzae* EXP03643 was precipitated with ammonium sulfate (80% saturation) and re-dissolved in 50 ml of 20 mM Tris-HCl pH 7.0, dialyzed against the same buffer, and filtered through a 0.45 mm filter. The final volume was 75 ml. The solution was applied to a 40 ml Q SEPHAROSE® Fast Flow column (GE Healthcare, Piscataway, N.J., USA) equilibrated in 20 mM Tris-HCl pH 7.0. The proteins were eluted with a linear 0-0.7 M NaCl gradient. Fractions eluted with 0.1-0.6 M NaCl were pooled and dialyzed against the same equilibration buffer. The dialyzed material was further purified on the same Q SEPHAROSE® Fast Flow column with a 0.1-0.5 M NaCl gradient. Fractions were evaluated by SDS-PAGE using a NUPAGE® NOVEX® 4-12% Bis-Tris Gel with MES. Fractions containing a band at approximately 70 kDa were pooled and the pooled solution was concentrated by ultrafiltration.

Example 9: Preparation of *Trichoderma reesei* GH5 Endoglucanase II

The *Trichoderma reesei* GH5 endoglucanase II (SEQ ID NO: 7 [DNA sequence] and SEQ ID NO: 8 [deduced amino acid sequence]) was prepared recombinantly according to WO 2011/057140 using *Aspergillus oryzae* as a host. The filtered broth of the *T. reesei* endoglucanase II was desalted and buffer-exchanged into 20 mM Tris pH 8.0 using a tangential flow concentrator (Pall Filtron, Northborough, Mass., USA) equipped with a 10 kDa polyethersulfone membrane (Pall Filtron, Northborough, Mass., USA). The protein concentration was determined using a Microplate BCA™ Protein Assay Kit (Thermo Fischer Scientific, Waltham, Mass., USA) in which bovine serum albumin was used as a protein standard.

Example 10: Preparation of *Aspergillus fumigatus* Cel3A Beta-Glucosidase

The *Aspergillus fumigatus* NN055679 Cel3A beta-glucosidase (SEQ ID NO: 9 [DNA sequence] and SEQ ID NO: 10 [deduced amino acid sequence]) was recombinantly prepared according to WO 2005/047499 using *Aspergillus oryzae* as a host. The filtered broth was adjusted to pH 8.0 with 20% sodium acetate, which made the solution turbid. To remove the turbidity, the solution was centrifuged at 20,000×g for 20 minutes, and the supernatant was filtered through a 0.2 μm filtration unit (Nalgene, Rochester, N.Y., USA). The filtrate was diluted with deionized water to reach the same conductivity as 50 mM Tris-HCl pH 8.0. The adjusted enzyme solution was applied to a Q SEPHAROSE® Fast Flow column equilibrated in 50 mM Tris-HCl pH 8.0 and eluted with a linear 0 to 500 mM sodium chloride gradient. Fractions were pooled and treated with 1% (w/v) activated charcoal to remove color from the beta-glucosidase pool. The charcoal was removed by filtration of the suspension through a 0.2 μm filtration unit. The filtrate was adjusted to pH 5.0 with 20% acetic acid and diluted 10 times with deionized water. The adjusted filtrate was applied to a SP SEPHAROSE® Fast Flow column (GE Healthcare, Piscataway, N.J., USA) equilibrated in 10 mM succinic acid pH 5.0 and eluted with a linear 0 to 500 mM sodium chloride gradient. Fractions were collected and analyzed for beta-glucosidase activity using p-nitrophenyl-beta-D-glucopyranoside as substrate. A p-nitrophenyl-beta-D-glucopyranoside stock solution was prepared by dissolving 50 mg of the substrate in 1.0 ml of DMSO. Just before use a substrate solution was prepared by mixing 100 μl of the stock solution with 4900 μl of 100 mM succinic acid, 100 mM HEPES, 100 mM CHES, 100 mM CABS, 1 mM $CaCl_2$, 150 mM KCl, 0.01% TRITON® X-100, pH 5.0 (assay buffer). A 200 μl volume of the substrate solution was dispensed into a tube and placed on ice followed by 20 μl of enzyme sample (diluted in 0.01% TRITON® X-100). The assay was initiated by transferring the tube to a thermomixer, which was set to an assay temperature of 37° C. The tube was incubated for 15 minutes on the thermomixer at its highest shaking rate (1400 rpm). The assay was stopped by transferring the tube back to the ice bath and adding 600 μl of Stop solution (500 mM $H_3BO_3$/NaOH pH 9.7). Then the tube was mixed and allowed to reach room temperature. A 200 μl of supernatant was transferred to a microtiter plate and the absorbance at 405 nm was read as a measure of beta-glucosidase activity. A buffer control was included in the assay (instead of enzyme). Fractions with beta-glucosidase activity were further analyzed by SDS-PAGE. Fractions, where only one band was seen on a Coomassie blue stained SDS-PAGE gel, were pooled as the purified product. The protein concentration was determined using a Microplate BCA™ Protein Assay Kit in which bovine serum albumin was used as a protein standard.

Example 11: Microcrystalline Cellulose Hydrolysis Assay

A 5% microcrystalline cellulose slurry was prepared by addition of 2.5 g of microcrystalline cellulose (AVICEL® PH101; Sigma-Aldrich, St. Louis, Mo., USA) to a graduated 50 ml screw-cap conical tube followed by approximately 40 ml of double-distilled water. The conical tube was then mixed thoroughly by shaking/vortexing, and adjusted to 50 ml total with double-distilled water and mixed again. Contents of the tube were then quickly transferred to a 100 ml beaker and stirred rapidly with a magnetic stirrer.

The hydrolysis of microcrystalline cellulose was conducted using 2.2 ml deep-well plates (Axygen, Union City, Calif., USA) in a total reaction volume of 1.0 ml. The hydrolysis was performed with 25 mg of the microcrystalline cellulose slurry (containing 100% cellulose) per ml of reaction. A 500 μl aliquot of the 5% microcrystalline cellulose slurry was pipetted into each well of the 2.2 ml deep-well plate using a 1000 μl micropipette with a wide aperture tip (end of tip cut off about 2 mm from the base). Each reaction was performed with and without the addition of catechol. In reactions not containing catechol, 200 μl of double-distilled water were added to each well. Then 100 μl of 500 mM ammonium acetate pH 5.0 containing 100 μM copper sulfate or 100 μl of 500 mM ammonium acetate pH 8.0 containing 100 μM copper sulfate were added to each well. An enzyme mixture consisting of *Trichoderma reesei* GH5 endoglucanase II (loaded at 2 mg protein per g cellulose) and *Aspergillus fumigatus* GH3 beta-glucosidase (loaded at 2 mg protein per g cellulose) was prepared and then added simultaneously to each well in a volume of 100 μl. An enzyme mixture containing the GH61 polypeptide (loaded at 5 mg protein per g cellulose) was then added to each well in a volume of 100 μl for a final volume of 1 ml in each reaction not containing catechol. In the reactions containing catechol, 200 μl of 100 mM catechol were added to each of the appropriate wells for a final volume of 1 ml and a final catechol concentration of 20 mM. The plate was then sealed using an ALPS-300™ plate heat sealer (Abgene, Epsom, United Kingdom), mixed thoroughly, and incubated at 50° C. for 72 hours. All experiments reported were performed in triplicate.

Following hydrolysis, samples were filtered using a 0.45 μm MULTISCREEN® 96-well filter plate (Millipore, Bedford, Mass., USA) and filtrates analyzed for sugar content as described below. When not used immediately, filtered aliquots were frozen at −20° C. The sugar concentrations of the samples were measured using a 4.6×250 mm AMINEX® HPX-87H column (Bio-Rad Laboratories, Inc., Hercules, Calif., USA) by elution with 0.05% w/w benzoic acid-0.005 M $H_2SO_4$ at 65° C. at a flow rate of 0.6 ml per minute, and quantitation by integration of the glucose signal from refractive index detection (CHEMSTATION®, AGILENT® 1100 HPLC, Agilent Technologies, Santa Clara, Calif., USA) calibrated by pure sugar samples.

Glucose was measured individually. All HPLC data processing was performed using MICROSOFT EXCEL™ software (Microsoft, Richland, Wash., USA). The resultant glucose equivalents were used for comparison of each reaction. Triplicate data points were averaged and standard deviation was calculated.

Example 12: Effect of the *Aspergillus niveus* GH61 Polypeptide on the Hydrolysis of Microcrystalline Cellulose The *Aspergillus niveus* GH61 polypeptide was evaluated for the ability to enhance the hydrolysis of microcrystalline cellulose in the presence of *Trichoderma reesei* GH5 endoglucanase II (loaded at 2 mg protein per g cellulose) and *Aspergillus fumigatus* GH3 beta-glucosidase (loaded at 2 mg protein per g cellulose) with and without the addition of 20 mM catechol at 50° C. The *Aspergillus niveus* GH61 polypeptide was added at 5 mg protein per g cellulose. The mixture of *T. reesei* GH5 endoglucanase II (loaded at 2 mg protein per g cellulose) and *A. fumigatus* GH3 beta-glucosidase (loaded at 2 mg protein per g cellulose) was also run as a control without added GH61 polypeptide.

The assay was performed as described in Example 11. The 1 ml reactions with microcrystalline cellulose were conducted for 72 hours in 50 mM ammonium acetate pH 5.0 containing 10 μM copper sulfate or 50 mM ammonium acetate pH 8.0 containing 10 μM copper sulfate. All reactions were performed in triplicate and involved single mixing at the beginning of hydrolysis.

Figure 2:
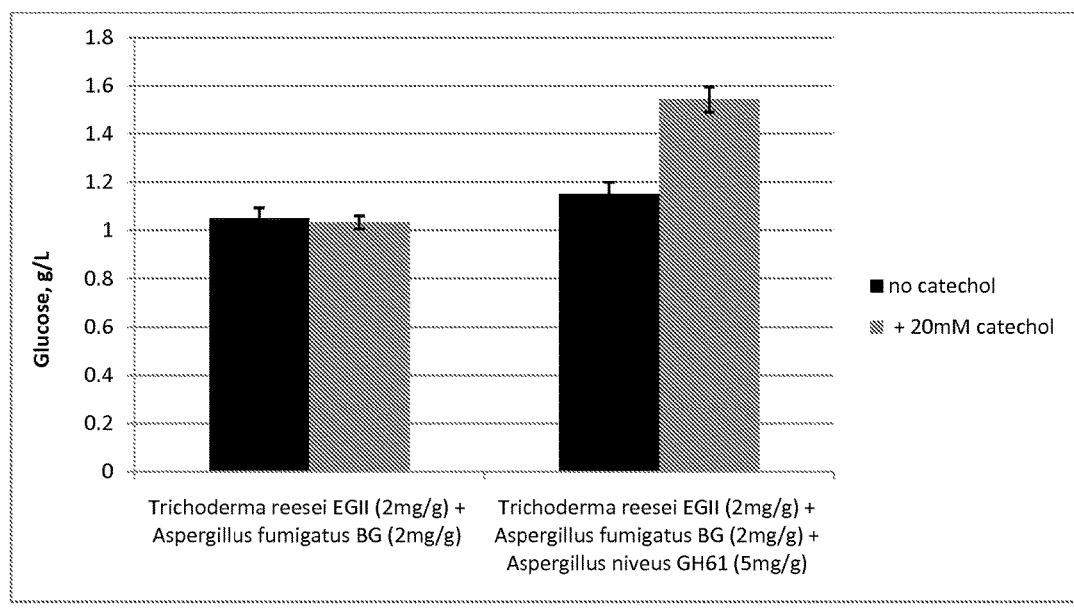
FIG. 2 shows the effect of the *Aspergillus niveus* GH61 polypeptide on the hydrolysis of microcrystalline cellulose by a cellulolytic enzyme composition at pH 5.0.
Figure 3:
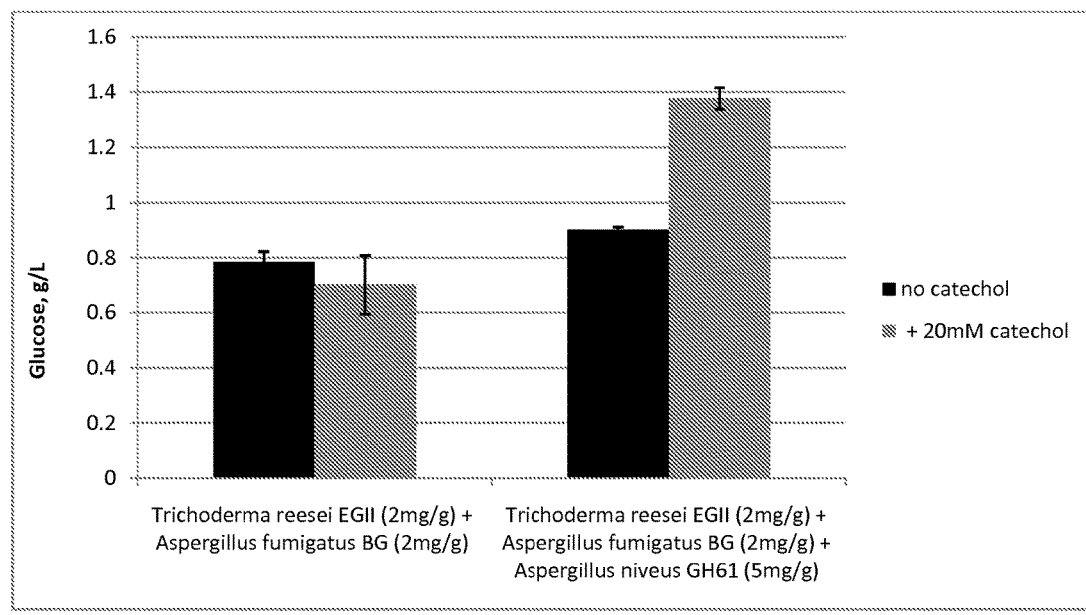
FIG. 3 shows the effect of the *Aspergillus niveus* GH61 polypeptide on the hydrolysis of microcrystalline cellulose by a cellulolytic enzyme composition at pH 8.0.

As shown in FIGS. 2 and 3, hydrolysis of the microcrystalline cellulose by the mixture of *T. reesei* GH5 endoglucanase II and *A. fumigatus* GH3 beta-glucosidase without catechol produced similar results as that obtained with the *A. niveus* GH61 polypeptide added to the mixture of *T. reesei* GH5 endoglucanase II and *A. fumigatus* GH3 beta-glucosidase without catechol. The addition of *A. niveus* GH61 polypeptide to the mixture of *T. reesei* GH5 endoglucanase II and *A. fumigatus* GH3 beta-glucosidase without catechol did not improve hydrolysis of the microcrystalline cellulose. However, as shown in FIGS. 2 and 3, the addition of *A. niveus* GH61 polypeptide to the mixture of *T. reesei* GH5 endoglucanase II and *A. fumigatus* GH3 beta-glucosidase with 20 mM catechol resulted in a higher degree of glucose production (shown in g/L) compared to the addition of *A. niveus* GH61 polypeptide to the mixture of *T. reesei* GH5 endoglucanase II and *A. fumigatus* GH3 beta-glucosidase without added catechol and compared to the mixture of *T. reesei* GH5 endoglucanase II and *A. fumigatus* GH3 beta-glucosidase without GH61 polypeptide and without added catechol. The results in FIG. 2 demonstrated a 1.34 improvement (or 34% increase) in hydrolysis of the microcrystalline cellulose by *A. niveus* GH61 polypeptide addition to the mixture of *T. reesei* GH5 endoglucanase II and *A. fumigatus* GH3 beta-glucosidase with catechol compared to without catechol at pH 5 and the results in FIG. 3 demonstrated a 1.53 improvement (or 53% increase) in hydrolysis of the microcrystalline cellulose by *A. niveus* GH61 polypeptide addition to the mixture of *T. reesei* GH5 endoglucanase II and *A. fumigatus* GH3 beta-glucosidase with catechol compared to without catechol at pH 8.

The present invention is further described by the following numbered paragraphs:

[1] An isolated polypeptide having cellulolytic enhancing activity, selected from the group consisting of: (a) a polypeptide having at least 75% sequence identity to the mature polypeptide of SEQ ID NO: 2; (b) a polypeptide encoded by a polynucleotide that hybridizes under at least high stringency conditions with the mature polypeptide coding sequence of SEQ ID NO: 1 or the full-length complement thereof; (c) a polypeptide encoded by a polynucleotide having at least 75% sequence identity to the mature polypeptide coding sequence of SEQ ID NO: 1; (d) a variant of the mature polypeptide of SEQ ID NO: 2 comprising a substitution, deletion, and/or insertion at one or more positions; and (e) a fragment of the polypeptide of (a), (b), (c), or (d) that has cellulolytic enhancing activity.

[2] The polypeptide of paragraph 1, having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2.

[3] The polypeptide of paragraph 1, which is encoded by a polynucleotide that hybridizes under high or very high stringency conditions with the mature polypeptide coding sequence of SEQ ID NO: 1 or the full-length complement thereof.

[4] The polypeptide of paragraph 1, which is encoded by a polynucleotide having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1.

[5] The polypeptide of any of paragraphs 1-4, comprising or consisting of SEQ ID NO: 2 or the mature polypeptide of SEQ ID NO: 2.

[6] The polypeptide of paragraph 5, wherein the mature polypeptide is amino acids 20 to 399 of SEQ ID NO: 2.

[7] The polypeptide of paragraph 1, which is a variant of the mature polypeptide of SEQ ID NO: 2 comprising a substitution, deletion, and/or insertion at one or more positions.

[8] The polypeptide of any of paragraphs 1-7, which is a fragment of SEQ ID NO: 2, wherein the fragment has cellulolytic enhancing activity.

[9] A composition comprising the polypeptide of any of paragraphs 1-8.

[10] An isolated polynucleotide encoding the polypeptide of any of paragraphs 1-8.

[11] A nucleic acid construct or expression vector comprising the polynucleotide of paragraph 10 operably linked to one or more control sequences that direct the production of the polypeptide in an expression host.

[12] A recombinant host cell comprising the polynucleotide of paragraph 10 operably linked to one or more control sequences that direct the production of the polypeptide.

[13] A method of producing the polypeptide of any of paragraphs 1-8, comprising: cultivating a cell, which in its wild-type form produces the polypeptide, under conditions conducive for production of the polypeptide.

[14] The method of paragraph 13, further comprising recovering the polypeptide.

[15] A method of producing a polypeptide having cellulolytic enhancing activity, comprising: cultivating the host cell of paragraph 12 under conditions conducive for production of the polypeptide.

[16] The method of paragraph 15, further comprising recovering the polypeptide.

[17] A transgenic plant, plant part or plant cell transformed with a polynucleotide encoding the polypeptide of any of paragraphs 1-8.

[18] A method of producing a polypeptide having cellulolytic enhancing activity, comprising: cultivating the transgenic plant or plant cell of paragraph 17 under conditions conducive for production of the polypeptide.

[19] The method of paragraph 18, further comprising recovering the polypeptide.

[20] A method of producing a mutant of a parent cell, comprising inactivating a polynucleotide encoding the polypeptide of any of paragraphs 1-8, which results in the mutant producing less of the polypeptide than the parent cell.

[21] A mutant cell produced by the method of paragraph 20.

[22] The mutant cell of paragraph 21, further comprising a gene encoding a native or heterologous protein.

[23] A method of producing a protein, comprising: cultivating the mutant cell of paragraph 21 or 22 under conditions conducive for production of the protein.

[24] The method of paragraph 23, further comprising recovering the protein.

[25] A double-stranded inhibitory RNA (dsRNA) molecule comprising a subsequence of the polynucleotide of paragraph 10, wherein optionally the dsRNA is an siRNA or an miRNA molecule.

[26] The double-stranded inhibitory RNA (dsRNA) molecule of paragraph 25, which is about 15, 16, 17, 18, 19, 20, 21, 22, 23, 24, 25 or more duplex nucleotides in length.

[27] A method of inhibiting the expression of a polypeptide having cellulolytic enhancing activity in a cell, comprising administering to the cell or expressing in the cell the double-stranded inhibitory RNA (dsRNA) molecule of paragraph 25 or 26.

[28] A cell produced by the method of paragraph 27.

[29] The cell of paragraph 28, further comprising a gene encoding a native or heterologous protein.

[30] A method of producing a protein, comprising: cultivating the cell of paragraph 28 or 29 under conditions conducive for production of the protein.

[31] The method of paragraph 30, further comprising recovering the protein.

[32] An isolated polynucleotide encoding a signal peptide comprising or consisting of amino acids 1 to 19 of SEQ ID NO: 2.

[33] A nucleic acid construct or expression vector comprising a gene encoding a protein operably linked to the polynucleotide of paragraph 32, wherein the gene is foreign to the polynucleotide encoding the signal peptide.

[34] A recombinant host cell comprising a gene encoding a protein operably linked to the polynucleotide of paragraph 32, wherein the gene is foreign to the polynucleotide encoding the signal peptide.

[35] A method of producing a protein, comprising: cultivating a recombinant host cell comprising a gene encoding a protein operably linked to the polynucleotide of paragraph 32, wherein the gene is foreign to the polynucleotide encoding the signal peptide, under conditions conducive for production of the protein.

[36] The method of paragraph 35, further comprising recovering the protein.

[37] A process for degrading a cellulosic material, comprising: treating the cellulosic material with an enzyme composition in the presence of the polypeptide having cellulolytic enhancing activity of any of paragraphs 1-8.

[38] The process of paragraph 37, wherein the cellulosic material is pretreated.

[39] The process of paragraph 37 or 38, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a catalase, a peroxidase, a protease, and a swollenin.

[40] The process of paragraph 39, wherein the cellulase is one or more enzymes selected from the group consisting of an endoglucanase, a cellobiohydrolase, and a beta-glucosidase.

[41] The process of paragraph 39, wherein the hemicellulase is one or more enzymes selected from the group consisting of a xylanase, an acetylxylan esterase, a feruloyl esterase, an arabinofuranosidase, a xylosidase, and a glucuronidase.

[42] The process of any of paragraphs 37-41, further comprising recovering the degraded cellulosic material.

[43] The process of paragraph 42, wherein the degraded cellulosic material is a sugar.

[44] The process of paragraph 43, wherein the sugar is selected from the group consisting of glucose, xylose, mannose, galactose, and arabinose.

[45] A process for producing a fermentation product, comprising: (a) saccharifying a cellulosic material with an enzyme composition in the presence of the polypeptide having cellulolytic enhancing activity of any of paragraphs 1-8; (b) fermenting the saccharified cellulosic material with one or more fermenting microorganisms to produce the fermentation product; and (c) recovering the fermentation product from the fermentation.

[46] The process of paragraph 45, wherein the cellulosic material is pretreated.

[47] The process of paragraph 45 or 46, wherein the enzyme composition comprises the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a catalase, a peroxidase, a protease, and a swollenin.

[48] The process of paragraph 47, wherein the cellulase is one or more enzymes selected from the group consisting of an endoglucanase, a cellobiohydrolase, and a beta-glucosidase.

[49] The process of paragraph 47, wherein the hemicellulase is one or more enzymes selected from the group consisting of a xylanase, an acetylxylan esterase, a feruloyl esterase, an arabinofuranosidase, a xylosidase, and a glucuronidase.

[50] The process of any of paragraphs 45-49, wherein steps (a) and (b) are performed simultaneously in a simultaneous saccharification and fermentation.

[51] The process of any of paragraphs 45-50, wherein the fermentation product is an alcohol, an alkane, a cycloalkane, an alkene, an amino acid, a gas, isoprene, a ketone, an organic acid, or polyketide.

[52] A process of fermenting a cellulosic material, comprising: fermenting the cellulosic material with one or more fermenting microorganisms, wherein the cellulosic material is saccharified with an enzyme composition in the presence of the polypeptide having cellulolytic enhancing activity of any of paragraphs 1-8.

[53] The process of paragraph 52, wherein the fermenting of the cellulosic material produces a fermentation product.

[54] The process of paragraph 53, further comprising recovering the fermentation product from the fermentation.

[55] The process of any of paragraphs 52-54, wherein the cellulosic material is pretreated before saccharification.

[56] The process of any of paragraphs 52-55, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a catalase, a peroxidase, a protease, and a swollen in.

[57] The process of paragraph 56, wherein the cellulase is one or more enzymes selected from the group consisting of an endoglucanase, a cellobiohydrolase, and a beta-glucosidase.

[58] The process of paragraph 56, wherein the hemicellulase is one or more enzymes selected from the group consisting of a xylanase, an acetylxylan esterase, a feruloyl esterase, an arabinofuranosidase, a xylosidase, and a glucuronidase.

[59] The process of any of paragraphs 53-58, wherein the fermentation product is an alcohol, an alkane, a cycloalkane, an alkene, an amino acid, a gas, isoprene, a ketone, an organic acid, or polyketide.

[60] A whole broth formulation or cell culture composition comprising the polypeptide of any of paragraphs 1-8.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A nucleic acid construct or expression vector comprising a polynucleotide encoding a GH61 polypeptide having cellulolytic enhancing activity, wherein the polynucleotide is operably linked to one or more heterologous control sequences that direct the production of the GH61 polypeptide in an expression host and wherein the GH61 polypeptide having cellulolytic enhancing activity has at least 95% sequence identity to the amino acid sequence of amino acids 20 to 399 of SEQ ID NO: 2.

2. A recombinant host cell transformed with the nucleic acid construct or the expression vector of claim 1.

3. A method of producing a GH61 polypeptide having cellulolytic enhancing activity, comprising: cultivating the recombinant host cell of claim 2 under conditions conducive for production of the polypeptide and optionally recovering the GH61 polypeptide.

4. A transgenic plant, plant part or plant cell transformed with the nucleic acid construct or the expression vector of claim 1.

5. A method of producing a GH61 polypeptide having cellulolytic enhancing activity, comprising: cultivating the transgenic plant or plant cell of claim 4 under conditions conducive for production of the polypeptide and optionally recovering the GH61 polypeptide.

6. A method of producing a mutant of a parent cell, comprising inactivating a polynucleotide encoding a GH61 polypeptide having cellulolytic enhancing activity, which results in the mutant producing less of the polypeptide than the parent cell, wherein the GH61 polypeptide having cellulolytic enhancing activity has at least 95% sequence identity to the amino acid sequence of amino acids 20 to 399 of SEQ ID NO: 2.

7. The nucleic acid construct or expression vector of claim 1, wherein the GH61 polypeptide has at least 96% sequence identity to the amino acid sequence of amino acids 20 to 399 of SEQ ID NO: 2.

8. The nucleic acid construct or expression vector of claim 1, wherein the GH61 polypeptide has at least 97% sequence identity to the amino acid sequence of amino acids 20 to 399 of SEQ ID NO: 2.

9. The nucleic acid construct or expression vector of claim 1, wherein the GH61 polypeptide has at least 98% sequence identity to the amino acid sequence of amino acids 20 to 399 of SEQ ID NO: 2.

10. The nucleic acid construct or expression vector of claim 1, wherein the GH61 polypeptide has at least 99% sequence identity to the amino acid sequence of amino acids 20 to 399 of SEQ ID NO: 2.

11. The nucleic acid construct or expression vector of claim 1, wherein the GH61 polypeptide comprises SEQ ID NO: 2 or the amino acid sequence of amino acids 20 to 399 of SEQ ID NO: 2.

12. The method of claim 6, wherein the GH61 polypeptide has at least 96% sequence identity to the amino acid sequence of amino acids 20 to 399 of SEQ ID NO: claim 2.

13. The method of claim 6, wherein the GH61 polypeptide has at least 97% sequence identity to the amino acid sequence of amino acids 20 to 399 of SEQ ID NO: claim 2.

14. The method of claim 6, wherein the GH61 polypeptide has at least 98% sequence identity to the amino acid sequence of amino acids 20 to 399 of SEQ ID NO: claim 2.

15. The method of claim 6, wherein the GH61 polypeptide has at least 99% sequence identity to the amino acid sequence of amino acids 20 to 399 of SEQ ID NO: claim 2.

16. The method of claim 6, wherein the GH61 polypeptide comprises SEQ ID NO: 2 or the amino acid sequence of amino acids 20 to 399 of SEQ ID NO: 2.

17. A recombinant host cell transformed with a nucleic acid construct or an expression vector comprising a polynucleotide encoding a GH61 polypeptide having cellulolytic enhancing activity, wherein the GH61 polypeptide is heterologous to the host cell and wherein the GH61 polypeptide having cellulolytic enhancing activity has at least 95% sequence identity to the amino acid sequence of amino acids 20 to 399 of SEQ ID NO: 2.

18. The recombinant host cell of claim 17, wherein the GH61 polypeptide has at least 96% sequence identity to the amino acid sequence of amino acids 20 to 399 of SEQ ID NO: 2.

19. The recombinant host cell of claim 17, wherein the GH61 polypeptide has at least 97% sequence identity to the amino acid sequence of amino acids 20 to 399 of SEQ ID NO: 2.

20. The recombinant host cell of claim 17, wherein the GH61 polypeptide has at least 98% sequence identity to the amino acid sequence of amino acids 20 to 399 of SEQ ID NO: 2.

21. The recombinant host cell of claim 17, wherein the GH61 polypeptide has at least 99% sequence identity to the amino acid sequence of amino acids 20 to 399 of SEQ ID NO: 2.

22. The recombinant host cell of claim 17, wherein the GH61 polypeptide comprises SEQ ID NO: 2 or the amino acid sequence of amino acids 20 to 399 of SEQ ID NO: 2.

23. A method of producing a GH61 polypeptide having cellulolytic enhancing activity, comprising: cultivating the recombinant host cell of claim 17 under conditions conducive for production of the polypeptide and optionally recovering the GH61 polypeptide.

* * * * *